United States Patent
Hoefer et al.

(10) Patent No.: US 11,478,424 B2
(45) Date of Patent: Oct. 25, 2022

(54) MECHANOCHEMCIAL ACTIVATED DRY AMORPHISATION BY MILLING EQUILIBRIUM BETWEEN AP MESOPOROUS SILICA

(71) Applicant: Grace GmbH, Columbia, MD (US)

(72) Inventors: Hans Hermann Hoefer, Westhofen (DE); Frederik Hendrik Monsuur, Hasselt (BE); Thomas Pauly, Wiesbaden (DE); Yogesh Choudhari, Secunderabad (IN); Korbinian Lobmann, Copenhagen (DK); Thomas Rades, Copenhagen (DK)

(73) Assignee: Grace GmbH, Columbia, MD (US)

( * ) Notice: Subject to any disclaimer, the term of this patent is extended or adjusted under 35 U.S.C. 154(b) by 0 days.

(21) Appl. No.: 15/765,115

(22) PCT Filed: Sep. 30, 2016

(86) PCT No.: PCT/EP2016/073488
§ 371 (c)(1),
(2) Date: Mar. 30, 2018

(87) PCT Pub. No.: WO2017/055591
PCT Pub. Date: Apr. 6, 2017

(65) Prior Publication Data
US 2018/0289621 A1    Oct. 11, 2018

Related U.S. Application Data

(60) Provisional application No. 62/235,101, filed on Sep. 30, 2015.

(51) Int. Cl.
| | | |
|---|---|---|
| A61K 9/14 | (2006.01) | |
| A61K 47/10 | (2017.01) | |
| A61K 47/20 | (2006.01) | |
| A61K 47/26 | (2006.01) | |
| A61K 47/32 | (2006.01) | |
| A23L 33/16 | (2016.01) | |
| A61K 31/192 | (2006.01) | |
| A61K 31/397 | (2006.01) | |
| C01B 33/18 | (2006.01) | |

(52) U.S. Cl.
CPC .............. A61K 9/143 (2013.01); A23L 33/16 (2016.08); A61K 31/192 (2013.01); A61K 31/397 (2013.01); A61K 47/10 (2013.01); A61K 47/20 (2013.01); A61K 47/26 (2013.01); A61K 47/32 (2013.01); C01B 33/18 (2013.01); A23V 2002/00 (2013.01); C01P 2004/50 (2013.01); C01P 2004/61 (2013.01); C01P 2006/12 (2013.01); C01P 2006/14 (2013.01); C01P 2006/16 (2013.01); C01P 2006/82 (2013.01)

(58) Field of Classification Search
CPC combination set(s) only.
See application file for complete search history.

(56) References Cited

U.S. PATENT DOCUMENTS

2011/0256184 A1    10/2011    Lei et al.

FOREIGN PATENT DOCUMENTS

| WO | 2012116238 | | 8/2012 | |
|---|---|---|---|---|
| WO | 2013110789 | | 8/2013 | |
| WO | WO-2014/034588 A1 | | 3/2014 | |
| WO | 2014078435 | | 5/2014 | |
| WO | WO 2014/078435 | * | 5/2014 | ............... A61K 9/48 |
| WO | 2015067603 | | 5/2015 | |
| WO | WO-2015/067682 A1 | | 5/2015 | |

OTHER PUBLICATIONS

Physicochemical Principles of Pharmacy, 5th Edition, p. 25, Alexander Florence and David Attwood, Pharmaceutical Press, 2011.*
Bahl et al. "Comparison of the Ability of Various Pharmaceutical Silicates to Amorphize and Enhance Dissolution of Indomethacin Upon Co-Grinding"; Pharmaceutical Development and Technology, 13, p. 255-269 (2008).
Choudhari et al. "Comparative Evaluation of Porous Silica Based Carriers for Lipids and Liquid Drug Formulations" Mesoporous Biomaterials, 1, p. 61-74 (2014).
Gaffet et al. "Crystal-Amorphous Phase Transition Induced by Ball-Milling in Silicon"; Journal of the Less-Common Metals, 157, p. 201-222 (1990).
Galarneau et al. "Pore-Shape Effects in Determination of Pore Size of Ordered Mesoporous Silicas by Mercury Intrusion."; Journal of Physical Chemistry C, 112, p. 12921-12927 (2008).
Gupta et al. "Formation of Physically Stable Amorphous Drugs by Milling with Neusilin"; Journal of Pharmaceutical Sciences, vol. 92, No. 3, p. 536-551 (2003).
Han et al. "Simultaneous Micronization and Surface Modification for Improvement of Flow and Dissolution of Drug Particles"; International Journal of Pharmaceutics, 415, p. 185-195 (2011).
Laitinen et al. "Emerging Trends in the Stabilization of Amorphous Drugs"; International Journal of Pharmaceutics, 453, p. 65-79 (2013).
Mallick et al. "Formation of Physically Stable Amorphous Phase of Ibuprofen by Solid State Milling with Kaolin." European Journal of Pharmaceutics and Biopharmaceutics, 68, p. 346-351 (2008).
Pan et al. "Increasing the Dissolution Rate of a Low-Solubility Drug Through a Crystalline-Amorphous Transition: A Case Study with Indomethicin"; Drug Development and Industrial Pharmacy, 34, p. 221-231 (2008).
Shen et al. "Physical State and Dissolution of Ibuprofen Formulated by Co-Spray Drying with Mesoporous Silica: Effect of Pore and Particle Size"; International Journal of Pharmaceutics, 410, p. 188-195 (2011).
Vogt et al. "A Solid-State NMR Study of Amorphous Ezetimibe Dispersions in Mesoporous Silica"; Pharmaceutical Research, 30, p. 2315-2331 (2013).

(Continued)

Primary Examiner — Hasan S Ahmed
(74) Attorney, Agent, or Firm — Foley & Lardner LLP

(57) ABSTRACT

Particles are disclosed. Methods of making and using the particles are also disclosed.

16 Claims, 17 Drawing Sheets

(56) References Cited

OTHER PUBLICATIONS

Watanabe et al. "Stability of Amorphous Indomethacin Compounded with Silica"; International Journal of Pharmaceutics, 226, p. 81-91 (2001).
Yang et al. "Effects of Amorphous Silicon Dioxides on Drug Dissolution"; Journal of Pharmaceutical Sciences, vol. 68, No. 5, p. 560-565 (1979).
Decision of Refusal on JP Application 2018-516829 dated May 12, 2021 (12 pages, English translation included).
Decision on Rejection on CN Application 201680069926.3 dated Jan. 17, 2022 (14 pages, English translation included).
European Communication pursuant to Article 94(3) EPC on EP Application No. 16778294.5 dated Mar. 15, 2022 (6 pages).
European Communication pursuant to Article 94(3) EPC on EP Application 16778294.5 dated Feb. 22, 2019 (6 pages).
Extended Hearing Notice on IN Application 201817014737 dated Dec. 20, 2021 (3 pages, English translation included).
Extended Hearing Notice on IN Application 201817014737 dated Nov. 22, 2021 (3 pages, English translation included).
First Examination Report on IN Application 201817014737 dated Mar. 3, 2020 (7 pages, English translation included).
First Office Action on CN Application 201680069926.3 dated Oct. 27, 2020 (12 pages, English translation included).
Hearing Notice on IN Application 201817014737 dated Nov. 1, 2021 (3 pages, English translation included).
Hearing Notice on IN Application 201817014737 dated Sep. 20, 2021 (3 pages, English translation included).
International Preliminary Report on Patentability on PCT/EP2016/073488 dated Apr. 3, 2018 (10 pages).
International Search Report and Written Opinion on PCT/EP2016/073488 dated Dec. 2, 2016 (14 pages).
Kinnari, P. et al., "Comparison of mesoporous silicon and non-ordered mesoporous silica materials as drug carriers for itraconazole," International Journal of Pharmaceutics, 414:148-156 (2011) (10 pages).
Krupa, et al., Preformulation Studies on Solid Self-Emulsifying Systems in Powder Form Containing Magnesium Aluminometasilicate as Porous Carrier; AAPS PharmSciTech., vol. 16, No. 3, pp. 623-635, Jun. 2015.
Notification of Reasons for Refusal on JP Application 2018-516829 dated Aug. 14, 2020 (10 pages, English translation included).
Preliminary Office Action on BR Application No. BR112018006660-5 dated Oct. 13, 2020 (9 pages, English translation included).
Reconsideration Report by Examiner before Appeal on JP Application 2018-516829, Appeal No. 2021-012193 dated Nov. 9, 2021 (9 pages, English translation included).
ScienceDirect article, www/sciencedirect.com/topics/medicine-and-dentistry/aerosil, May 2020.
Second Office Action on CN Application 201680069926.3 dated Jul. 14, 2021 (13 pages, English translation included).

\* cited by examiner

Syloid®244 FP as is, Resolution 1000

Syloid®244 FP 30HZ 60min, Resolution 1000

Syloid®244 XDP3050 as is, Resolution 1000

Syloid® XDP 3050 30HZ 60min Resolution 1000

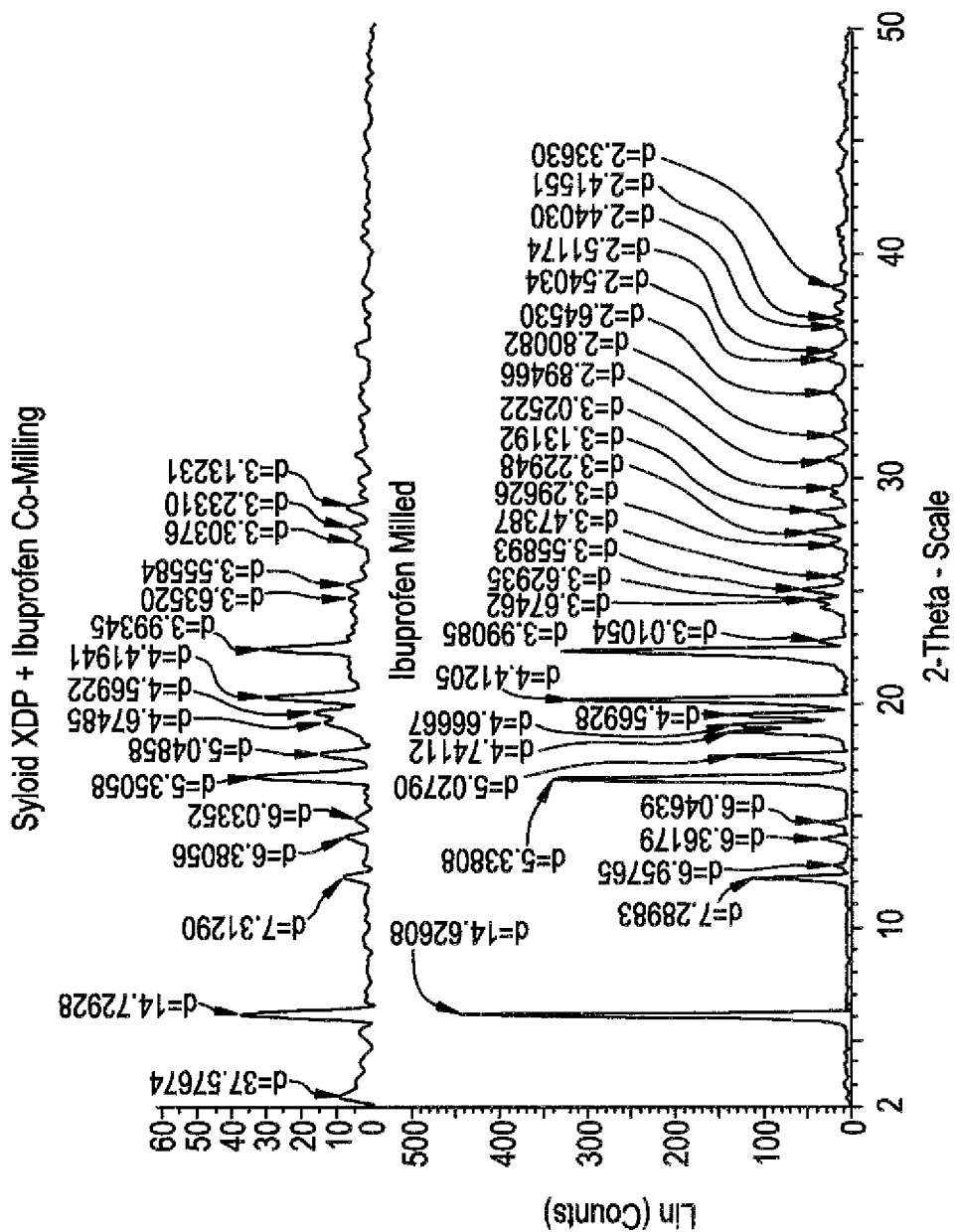

Effect of Comp Force on Tablet Dissolution

Effect of Milling Time on Drug Release @ pH 4.5

Syloid® 244 FP + IBU 3:1 30HZ 30min

Syloid® XDP+ IBU 3:1 30HZ 30min

Dissolution profile for Ibuprofen formulations prepared with Syloid®

Ibuprofen Dissolution Profile (50mg Dose)

Eze : XDP3050 1:1 20min 20Hz

Eze : XDP3050 1:5 5min 20Hz

US 11,478,424 B2

MECHANOCHEMCIAL ACTIVATED DRY AMORPHISATION BY MILLING EQUILIBRIUM BETWEEN AP MESOPOROUS SILICA

FIELD OF THE INVENTION

The present invention is directed to particles suitable for use as a delivery agent for an active ingredient (e.g., a drug) in a variety of processing including, but not limited to, drug delivery. The present invention is further directed to methods of making and using particles.

BACKGROUND

Efforts continue to develop porous particles that are suitable for use as a delivery agent in a variety of processing including, but not limited to, drug delivery.

SUMMARY

The present invention addresses a need in the art by the discovery of new porous inorganic particles and methods of making and using new particles. The particles of the present invention unexpectedly provide exceptional active ingredient dissolution properties when compared to known active ingredient (e.g., drug) delivery materials. The particles of the present invention may be prepared without the use of an organic solvent. Consequently, the resulting particles do not have concerns relating to possible residual solvent remaining within the particle, for example, in cases wherein the particle is utilized as a drug delivery mechanism. In addition, the disclosed methods of making particles of the present invention enable achievement of a particle equilibrium within minutes as opposed to hours or days without processing concerns associated with the use and handling of organic solvents.

Accordingly, the present invention is directed to porous inorganic particles. In one exemplary embodiment, the particles of the present invention comprise porous inorganic particles having (i) a total pore volume of less than 1.0 cc/gm, as determined by mercury intrusion porosimetry, and (ii) an intra-particle pore volume of less than 0.3 cc/gm, as determined by mercury intrusion porosimetry, wherein the intra-particle pores are defined as pores having a pore size of less than or equal to 2200 Å.

In a preferred embodiment, the particles of the present invention comprises porous inorganic oxide particles having (i) a total pore volume of less than 1.0 cc/gm, as determined by mercury intrusion porosimetry, and (ii) an intra-particle pore volume of less than 0.3 cc/gm, as determined by mercury intrusion porosimetry, wherein the intra-particle pores are defined as pores having a pore size of less than or equal to 2200 Å.

In another exemplary embodiment, the particles of the present invention comprise composite particles comprising porous inorganic particles, preferably porous inorganic oxide particles, and at least one active ingredient mechanically incorporated in pores of the inorganic oxide particles, wherein the composite particles have (i) a total pore volume of less than 1.0 cc/gm, as determined by mercury intrusion porosimetry, and (ii) an intra-particle pore volume of less than 0.3 cc/gm, as determined by mercury intrusion porosimetry, and wherein the intra-particle pores are defined as pores having a pore size of less than or equal to 2200 Å.

The present invention is further directed to methods of making porous inorganic particles in accordance with the invention. The method of making the particles of the invention generally comprises providing initial porous inorganic particles having a total pore volume, decreasing the total pore volume of the initial porous inorganic particles by subjecting the particles to sufficient mechanical force in a dry, soventless environment to achieve particle equilibrium and form newly exposed internal inorganic particle surfaces, and thereafter allowing consolidation or re-agglomeration of at least a portion of the mechanically treated porous inorganic particles so as to provide newly formed porous inorganic particles having a total pore volume that is different than the total pore volume of the initial porous inorganic particles. The total pore volume of the newly formed porous inorganic particles may be smaller or larger than the total pore volume of the initial porous inorganic particles. In a preferred embodiment, the newly formed porous inorganic particles have a total pore volume that is smaller than the total pore volume of the initial porous inorganic particles.

In one exemplary embodiment, the method of making particles of the present invention comprises a method of preparing porous inorganic particles, the method comprising: providing porous inorganic particles having an total pore volume of greater than 1.0 cc/gm, as measured by mercury intrusion porosimetry (i.e. any value greater than 1.0 cc/gm up to and including 10.0 cc/gm, in increments of 0.01 cc/gm, e.g., 6.00 cc/gm, or any range of values between greater than 1.0 cc/gm up to and including 10.0 cc/gm, in increments of 0.01 cc/gm, e.g., from about 1.01 cc/gm to about 9.99 cc/gm), as determined by mercury intrusion porosimetry, and (ii) an intra-particle pore volume of less than 3.0 cc/gm (or any value greater than 0 cc/gm up to and including 3.0 cc/gm, in increments of 0.01 cc/gm, e.g., 1.7 cc/gm, or any range of values between greater than 1.0 cc/gm up to and including 3.0 cc/gm, in increments of 0.01 cc/gm, e.g., from about 1.01 cc/gm to about 2.99 cc/gm), as determined by mercury intrusion porosimetry, wherein the intra-particle pores are defined as pores having a pore size of less than or equal to 2200 Å); and subjecting the particles in a dry, soventless environment to sufficient mechanical force to form porous inorganic particles having a total pore volume to less than or equal to 1.0 cc/gm, as determined by mercury intrusion porosimetry, and an intra-particle pore volume of less than 0.3 cc/gm, as determined by mercury intrusion porosimetry, wherein the intra-particle pores are defined as pores having a pore size of less than or equal to 2200 Å. In a preferred method the porous inorganic particles are porous inorganic oxide particles.

In another exemplary embodiment, the method of making particles of the present invention comprises a method of making composite porous inorganic particles comprising at least one active ingredient. The method comprising: providing (i) initial porous inorganic particles having a total pore volume and (ii) at least on active ingredient; and subjecting the particles and active ingredient in a dry, soventless environment to mechanical force in an amount sufficient to achieve particle equilibrium and form newly exposed internal inorganic particle surfaces, and thereafter allowing consolidation or re-agglomeration of at least a portion of the surfaces of the mechanically treated porous inorganic particles so as to provide composite inorganic particles having active ingredient mechanically incorporated into the pores thereof, wherein said composite particles have a total pore volume different than the total pore volume of the initial porous inorganic particles. The total pore volume of the newly formed composite particles may be smaller or larger than the total pore volume of the initial porous inorganic particles. In a preferred embodiment, the newly formed composite particles have a total pore volume that is smaller than the total pore volume of the initial porous inorganic particles In one exemplary embodiment, the method of making the composite particles comprises: providing porous inorganic particles having an total pore volume of greater than 1.0 cc/gram, as measured by mercury intrusion porosimetry; and subjecting the particles and at least one active ingredient in a dry, soventless environment to mechanical force in an amount sufficient to form porous composite inorganic particles having the at least one active ingredient incorporated into pores of the thereof, wherein the composite inorganic particles have a total pore volume to less than or equal to 1.0 cc/gm, as determined by mercury intrusion porosimetry, and an intra-particle pore volume of less than 0.3 cc/gm, as determined by mercury intrusion porosimetry, wherein the intra-particle pores are defined as pores having a pore size of less than or equal to 2200 Å.

The present invention is further directed to the use of porous inorganic particles in a variety of processes. In one exemplary embodiment, the present invention is directed to the use of the particles as an agent for delivering at least one active ingredient into an environment, the particles comprising porous inorganic particles having (i) a total pore volume of less than 1.0 cc/gm, as determined by mercury intrusion porosimetry, and (ii) an intra-particle pore volume of less than 0.3 cc/gm, as determined by mercury intrusion porosimetry, wherein the intra-particle pores are defined as pores having a pore size of less than or equal to 2200 Å.

In another exemplary embodiment, the present invention is directed to the use of composite particles as an agent for delivering at least one active ingredient into an environment, the composite particles comprising: (i) inorganic particles, and (ii) at least one active ingredient mechanically incorporated in pores of the inorganic particles, wherein the composite particles have (i) a total pore volume of less than 1.0 cc/gm, as determined by mercury intrusion porosimetry, and (ii) an intra-particle pore volume of less than 0.3 cc/gm, as determined by mercury intrusion porosimetry.

In some desired embodiments, the porous particles of the present invention are used as a drug delivery agent. The disclosed particles have been found to unexpectedly provide exceptional delivery of drugs for therapeutic applications, particularly, drugs having a relatively low solubility in water as measured by dissolution of the drug into an aqueous solution. In other desired embodiments, the particles are used as an active delivery agent in various areas including, but not limited to, the delivery of an active ingredient in dental or oral care, skin care, cosmetics, nutritional, agrochemical and plant and catalytic applications, etc.

These and other features and advantages of the present invention will become apparent after a review of the following detailed description of the disclosed embodiments and the appended claims.

BRIEF DESCRIPTION OF THE DRAWINGS

FIG. 4 graphically show X-ray diffraction study data for ibuprofen milled alone versus ibuprofen co-milled with SYLOID® XDP silica as described in Example 1 below;

DETAILED DESCRIPTION

Figure 1:
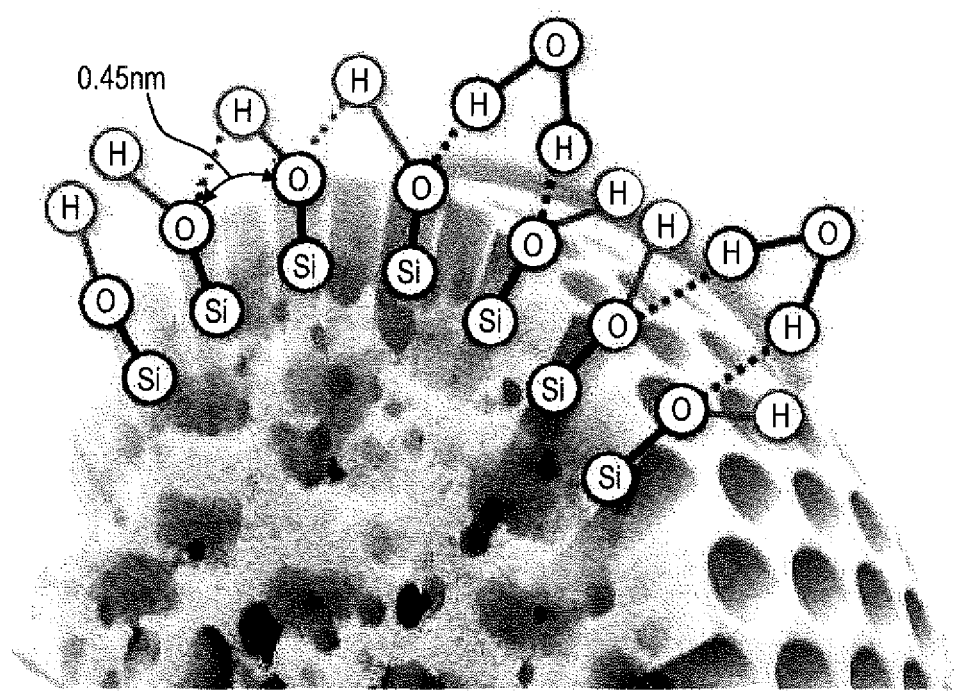
FIG. 1 graphically shows surface functional groups of silica particles.

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

It must be noted that as used herein and in the appended claims, the singular forms "a", "and", and "the" include plural referents unless the context clearly dictates otherwise. Thus, for example, reference to "an oxide" includes a plurality of such oxides and reference to "oxide" includes reference to one or more oxides and equivalents thereof known to those skilled in the art, and so forth.

"About" modifying, for example, the quantity of an ingredient in a composition, concentrations, volumes, process temperatures, process times, recoveries or yields, flow rates, and like values, and ranges thereof, employed in describing the embodiments of the disclosure, refers to variation in the numerical quantity that may occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

As used herein, the phrase "total pore volume" refers to the combination of (1) inter-particle pore volume (i.e., the volume between particles) and (2) intra-particle pore volume (i.e., the pore volume within the particles) for a plurality of particles. Typically, many, if not all, of the "particles" within the plurality of particles comprise a cluster of particles that have been mechanically combined with one another via a particle consolidation step such as a ball milling or jet milling or extruding step. Consequently, many, individual "particles" within the plurality of particles have both inter-particle pore volume and intra-particle pore volume. In addition, the plurality of particles also have inter-particle pore volume between the individual "particles" within the plurality of particles.

As used herein, the phrase "inter-particle pore volume" refers to the volume between particles within a plurality of particles. As noted above, "inter-particle pore volume" includes (1) the pore volume within individual "particles" (i.e., the pore volume between particles from into a cluster of particles), and (2) the pore volume between individual "particles."

As used herein, the phrase "intra-particle pore volume" refers to the pore volume within intra-particle pores of the particles of the plurality of particles. As used herein, "intra-particle pores" are defined as pores having a pore size of less than or equal to 2200 Å.

As used herein, the phrase "dry, soventless environment" refers to an environment free of solvent (i.e., any intentionally added solvent) and typically free of any liquid. A "dry, soventless environment" may comprise some degree of humidity and/or water presence within the "dry, soventless environment," but the humidity and/or water is present as a contaminant, not as a component added by a user.

As used herein, the phrase "newly exposed internal inorganic particle surfaces" refers to previously unexposed internal surfaces of inorganic particles that are exposed via the herein-described mechanical step (e.g., via a milling or extruding step) to decrease the pore volume. The phrase "newly exposed internal inorganic particle surfaces" does not refer to internal pore surfaces of inorganic particles such as internal pores surfaces of metal oxide particles. Likewise, as used herein, the phrase "newly exposed internal active ingredient particle surfaces" refers to previously unexposed internal surfaces of active ingredient particles that are exposed via the herein-described decreasing step (e.g., via a milling or extruding step).

As used herein, "inorganic oxides" is defined as binary oxygen compounds where the inorganic component is the cation and the oxide is the anion. The inorganic material includes metals and may also include metalloids. Metals include those elements on the left of the diagonal line drawn from boron to polonium on the periodic table. Metalloids or semi-metals include those elements that are on the right of this line. Examples of inorganic oxides include silica, alumina, titania, zirconia, etc., and mixtures thereof.

As used herein, "porous inorganic particles" includes particles comprised of inorganic materials, or combinations of inorganic materials (e.g., metals, semi-metals, and their alloys; ceramics, including inorganic oxides; etc.) and organic materials (e.g., organic polymers), such as composite materials, which are heterogeneous or homogeneous in nature. For example, heterogeneous composite materials include mere mixtures of materials, layered materials, core-shell, and the like. Examples of homogeneous composite materials include alloys, organic-inorganic polymer hybrid materials, and the like. The particles may be a variety of different symmetrical, asymmetrical or irregular shapes, including chain, rod or lath shape. The particles may have different structures including amorphous or crystalline, etc. The particles may include mixtures of particles comprising different compositions, sizes, shapes or physical structures, or that may be the same except for different surface treatments. Porosity of the particles may be intraparticle or interparticle in cases where smaller particles are agglomerated to form larger particles. In one exemplary embodiment, the particles are composed of inorganic materials such as inorganic oxides, sulfides, hydroxides, carbonates, silicates, phosphates, etc., but are desirably inorganic oxides, which may be formed via any known process including, but not limited to, solution polymerization such as for forming colloidal particles, continuous flame hydrolysis such as for forming fumed particles, gelation such as for forming gelled particles, precipitation, spraying, templating, sol-gel, and the like.

The inorganic particles may be processed according to the present invention as is or modified, prior to processing (i.e., a mechanical step), by autoclaving, flash drying, super critical fluid extracting, etching, or like processes. The inorganic particles may be composed of organic and/or inorganic materials and combinations thereof. In one exemplary embodiment the inorganic particles are composed of inorganic materials such as inorganic oxides, sulfides, hydroxides, carbonates, silicates, phosphates, etc., but are preferably inorganic oxides. The inorganic particles may be a variety of different symmetrical, asymmetrical or irregular shapes, including chain, rod or lath shape. The inorganic particles may have different structures including amorphous or crystalline, etc. The inorganic particles may include mixtures of particles comprising different compositions, sizes, shapes or physical structures, or that may be the same except for different surface treatments. Porosity of the inorganic particles may be intraparticle and/or interparticle in cases where smaller particles are agglomerated to form larger particles. In one exemplary embodiment the inorganic particles are composed of inorganic materials such as inorganic oxides, sulfides, hydroxides, carbonates, silicates, phosphates, etc., but are preferably inorganic oxides. Suitable porous inorganic oxide particle materials include organic and inorganic materials, or hybrids thereof.

As used herein, the term "crystalline" means a solid material whose constituent atoms, molecules, or ions are arranged in an ordered pattern extending in all three directions, which may be measured by X-ray diffraction or differential scanning calorimetry.

As used herein, the term "amorphous" means a solid material whose constituent atoms, molecules, or ions are arranged in a random, non-ordered pattern extending in all three directions, which may be determined by X-ray diffraction or differential scanning calorimetry.

As used herein, the phrase "particle equilibrium" refers to a point in time at which a given particle (or agglomeration of particles) undergoes an in situ amorphisation from a crystalline state into an amorphous state. The "particle equilibrium" takes place once a threshold amount of energy (e.g., frictional energy in the form of (i) particle-to-particle friction, as well as (ii) particle-to-equipment friction) is introduced into a given reaction vessel (e.g., a milling vessel or an extrusion vessel) containing the particle components. For example, in some embodiments, the "particle equilibrium" occurs when the stress and strain introduced rates of grinding/extruding equal the stress and strain introduced rates of compacting (i.e., final particle formation) when the applied mechanical agitation conditions are kept constant. In some embodiments, "particle equilibrium" is represented by a particle state and time in which particles having an initial average particle size have been exposed to a desired amount of mechanical agitation so as to (1) cause an initial decrease in the initial average particle size, and (2) subsequently cause consolidation of resulting smaller particles having newly exposed particle surfaces so as to form final particles having a final average particle size that, in many case, is larger than the initial average particle size.

As used herein, the term "pore size distribution" means the relative abundance of each pore size in a representative volume of porous inorganic particles. As used herein "median pore size" is the pore diameter below which 50% of the intraparticle pore volume resides for pores between 20 and 600 angstroms. Pore size distributions may be measured, for example, by mercury intrusion using an Autopore IV 9520 available from Micromeritics Instrument Corp.

As used herein, the term "active ingredient" includes, but is not limited to, an active pharmaceutical ingredient (API), an agricultural component (e.g., pesticide, fungicide, herbicide, fertilizer, etc.), a food or feed component (e.g., nutrient, vitamin, etc.), or any combination thereof. In some desired embodiments, the "active ingredient" comprises an active pharmaceutical ingredient (API), which provides a pharmacological activity or otherwise have direct effect in the diagnosis, cure, mitigation, treatment or prevention of disease, or to have direct effect in restoring, correcting or modifying physiological functions in humans. Even though this includes poorly soluble material, it may also include materials that range in solubility, including those listed in the BCS (Biopharmaceutical Classification System), which is a classification approach where drugs (APS) are divided in to four classes based on the extent (high or low) of their aqueous solubility and permeability through the GI tract wall, in particular intestinal. In this regard, these four classes are: (Group I) High Solubility and High Permeability drugs, (Group II) Low Solubility and High Permeability drugs, (Group III) High Solubility and Low Permeability drugs, and (Group IV) Low solubility and Low Permeability drugs.

As used herein, the term "dissolution" means the process by which a solid, liquid or a gas forms a solution in a solvent. For dissolution of solids, the process involves the breakdown of the crystal lattice and/or solid structure into individual ions, atoms or molecules and their transport into the solvent. Dissolution rates of a biologically active material (e.g., API) are a measure of drug release to determine in vivo bioavailability.

As used herein, the term "BET particle surface area" is defined as meaning a particle surface area as measured by the Brunauer Emmett Teller nitrogen adsorption method.

As used herein, the term "molecular weight" is defined as meaning the molar mass of a single molecule of a particular compound or polymer.

As discussed in the embodiments below, the porous inorganic particles may comprise a variety of inorganic materials including, but not limited to, magnesium aluminosilicate, calcium phosphate, calcium carbonate, and inorganic oxides, such as for example, silica, alumina, zirconia, controlled pore glass, or mixtures thereof. In one desired embodiment, the inorganic oxide particles comprise silica. Suitable silica includes, but is not limited to, silica gel, precipitated silica, fumed silica and colloidal silica. Suitable silica also includes, but is not limited to, ordered mesoporous silica prepared through an organic template (e.g., a surfactant) during the formation of silica particles, followed by a high temperature pyrolysis to "burn off" the organics. When the inorganic oxide particles comprise silica, the particles desirably comprise silica having a purity of at least about 93.0% by weight $SiO_2$, or at least about 93.5% by weight $SiO_2$, at least about 94.0% by weight $SiO_2$, at least about 95.0% by weight $SiO_2$, at least about 96.0% by weight $SiO_2$, at least about 97.0% by weight $SiO_2$, or at least about 98.0% by weight $SiO_2$ up to 100% by weight $SiO_2$ based upon the total weight of the particle.

The active ingredient used in the compositions of the present invention may comprise any known active ingredient. In some embodiments, the active ingredient comprises at least one active pharmaceutical ingredient (API). In some embodiments, the active ingredient comprises two or more active pharmaceutical ingredients (APIs) in combination with one another. In some embodiments, the APIs include those of Groups II or IV of the Biopharmaceutics Classification System (BCS) (FDA). Exemplary APIs include, but are not limited to, atorvastatin, amiodarone, candesartan-cilexetil, carvedilol, clopidogrel bisulfate, dipyridamole, eposartan mesylate, epierenone, ezetimibe, felodipme, furosemide, isradipine, lovastatin, metolazone, nicardipine, nisoldipine olmesartan medoxomil, propafenone HCl, ginapril, ramipril, simvastatin, telmisartan, trandolapril, valsartan and other cardio-vascular active drugs; acyclovir, adefovir, dipivoxil, amphotericin, amprenavir, cefixime, ceflazidime, clarithromycin, clotrimazole, efavirenz, ganciclovir, itracnazole, norfloxcin, nystatin ritonavir, saquinavir and other anti-infective drugs including anti-bacterial, antiviral, anti-fungal and anti-parasitic drugs; cisplatin, carboplatin, docetaxel, etoposide, exemestane, idarubicin, irinotecan, melphalan, mercaptopurine, mitiane, paclitaxel, valrubicin, vincristine and other drugs used in oncology; azthioprine, tacrolimus, cyclosporine, pimecrolimus, sirolimus and other immonosupressive drugs; clozapine, entacapone, fluphenazine, imipramine, nefazodone, olanzapine, paroxetine, pimoxide sertraline, triazolam, zaleplon, siprasidon eand, risperidone, carbanazepine and other drugs for CNS indications; danazol, dutasteride, medroxyprogesterone, estradiol, raloxifene, sildenafil, tadalafil, testosterone, vardenafil and other drugs used for reproductive health; celecoxib, dihydroergotamine mesylate, eletriptan, ergoloidmesylates, ergotamine-tartrate, nabumetone, ibuprofen, ketoprofen, triamcinolone, triamcinolone acetonide and other anti-inflammatory and analgesic drugs; bosentan, budesonide, desloratadine, fexofenadin, fluticasone, loratadine, mometasone, salmeterol xinafoate, triamcinolon acetonide, zafirlukast and other drugs for respiratory indications; and dronabinol, famotidine, glyburide, hyoscyramine, isotretinoin, megestrol, mesalamine, modafinil, mosapride, nimodipine, perphenazine, propofol, sucralfate, thalidomide, trizaidiline hydrochloride and other drugs for various indications including in particular gastrointestinal disorders, diabetes and dermatology indications. In further embodiments, the APIs include ezetimibe glucoroniude, tadalafil, fenofibrate, danazol, itraconazol, carbamazepine, griseofulvin, nifedipin, or any combination thereof.

Further additional embodiments of the present invention are described below. It should be noted that the recitation of numerical ranges by endpoints in any of the embodiments disclosed herein includes all numbers subsumed within that range (e.g., the range about 1 to about 5 includes 1, 1.5, 2, 2.75, 3, 3.80, 4, and 5) and any range within that range (e.g., the range of about 1.5 to about 3.78 within the range of 1 to 5).

ADDITIONAL EMBODIMENTS

Porous Inorganic Particles

Porous inorganic particles having (i) a total pore volume of less than 1.0 cc/gm (or any value greater than 0 cc/gm up to and including 1.0 cc/gm, in increments of 0.01 cc/gm, e.g., 0.32 cc/gm, or any range of values between greater than 0 cc/gm up to and including 1.0 cc/gm, in increments of 0.01 cc/gm, e.g., from about 0.30 cc/gm to about 0.34 cc/gm), as determined by mercury intrusion porosimetry, and (ii) an intra-particle pore volume of less than 0.3 cc/gm (or any value greater than 0 cc/gm up to and including 0.3 cc/gm, in increments of 0.01 cc/gm, e.g., 0.09 cc/gm, or any range of values between greater than 0 cc/gm up to and including 0.3 cc/gm, in increments of 0.01 cc/gm, e.g., from about 0.09 cc/gm to about 0.11 cc/gm), as determined by mercury intrusion porosimetry, wherein the intra-particle pores are defined as pores having a pore size of less than or equal to 2200 Å. Preferably, the inorganic particles are porous inorganic oxide particles.

The porous inorganic particles of embodiment 1, wherein the particles have (i) a total pore volume of greater than 0 and less than about 0.98 cc/gm, as determined by mercury intrusion porosimetry, and (ii) an intra-particle pore volume of greater than 0 and less than about 0.28 cc/gm, as determined by mercury intrusion porosimetry.

The porous inorganic particles of embodiment 1 or 2, wherein the particles have (i) a total pore volume of from about 0.15 to about 0.93 cc/gm, as determined by mercury intrusion porosimetry, and (ii) an intra-particle pore volume of from about 0.05 to about 0.24 cc/gm, as determined by mercury intrusion porosimetry.

The porous inorganic particles of any one of embodiments 1 to 3, wherein the particles have (i) a total pore volume of from about 0.25 to about 0.40 cc/gm, as determined by mercury intrusion porosimetry, and (ii) an intra-particle pore volume of from about 0.08 to about 0.16 cc/gm, as determined by mercury intrusion porosimetry.

The porous inorganic particles of any one of embodiments 1 to 4, wherein the particles have an average particle size of from about 1.0 micron (μm) to about 100 μm (or any value between and including 1.0 μm to about 100 μm, in increments of 0.1 μm, e.g., 45.0 μm, or any range of values between and including 1.0 μm to about 100 μm, in increments of 0.1 μm, e.g., from about 3.2 μm to about 50.1 μm).

The porous inorganic particles of any one of embodiments 1 to 5, wherein the particles have an average particle size of from about 2.0 μm to about 60 μm.

The porous inorganic particles of any one of embodiments 1 to 6, wherein the particles have an average particle size of from about 40.0 μm to about 50.0 μm.

The porous inorganic particles of any one of embodiments 1 to 7, wherein the particles comprise an agglomeration of mechanically altered inorganic particles having newly exposed internal inorganic particle surfaces thereon.

Composite Particles

Composite particles comprising the porous, inorganic particles of any one of embodiments 1 to 8 and at least one active ingredient mechanically incorporated in pores of the inorganic particles, wherein the composite particles have (i) a total pore volume of less than 1.0 cc/gm, as determined by mercury intrusion porosimetry, and (ii) an intra-particle pore volume of less than 0.3 cc/gm, as determined by mercury intrusion porosimetry. Preferably, the porous particles are porous, inorganic oxide particles.

Composite particles comprising porous, inorganic particles and at least one active ingredient mechanically incorporated in pores of the inorganic particles, wherein the composite particles have (i) a total pore volume of less than 1.0 cc/gm (or any value greater than 0 cc/gm up to and including 1.0 cc/gm, in increments of 0.01 cc/gm, e.g., 0.32 cc/gm, or any range of values between greater than 0 cc/gm up to and including 1.0 cc/gm, in increments of 0.01 cc/gm, e.g., from about 0.30 cc/gm to about 0.34 cc/gm), as determined by mercury intrusion porosimetry, and (ii) an intra-particle pore volume of less than 0.3 cc/gm (or any value greater than 0 cc/gm up to and including 0.3 cc/gm, in increments of 0.01 cc/gm, e.g., 0.09 cc/gm, or any range of values between greater than 0 cc/gm up to and including 0.3 cc/gm, in increments of 0.01 cc/gm, e.g., from about 0.09 cc/gm to about 0.11 cc/gm), as determined by mercury intrusion porosimetry, and wherein the intra-particle pores are defined as pores having a pore size of less than or equal to 2200 Å.

The composite particles of embodiment 10, wherein the composite particles have (i) a total pore volume of greater than 0 and less than about 0.98 cc/gm, as determined by mercury intrusion porosimetry, and (ii) an intra-particle pore volume of greater than 0 and less than about 0.28 cc/gm, as determined by mercury intrusion porosimetry.

The composite particles of embodiment 10 or 11, wherein the composite particles have (i) a total pore volume of from about 0.15 to about 0.93 cc/gm, as determined by mercury intrusion porosimetry, and (ii) an intra-particle pore volume of from about 0.05 to about 0.24 cc/gm, as determined by mercury intrusion porosimetry.

The composite particles of any one of embodiments 10 to 12, wherein the composite particles have (i) a total pore volume of from about 0.25 to about 0.40 cc/gm, as determined by mercury intrusion porosimetry, and (ii) an intra-particle pore volume of from about 0.08 to about 0.16 cc/gm, as determined by mercury intrusion porosimetry.

The composite particles of any one of embodiments 10 to 13, wherein the composite particles have an average particle size of from about 1.0 μm to about 100 μm (or any value between and including 1.0 µm to about 100 µm, in increments of 0.1 µm, e.g., 45.0 µm, or any range of values between and including 1.0 µm to about 100 µm, in increments of 0.1 µm, e.g., from about 3.2 µm to about 50.1 µm).

The composite particles of any one of embodiments 10 to 14, wherein the composite particles have an average particle size of from about 2.0 µm to about 60 µm.

The composite particles of any one of embodiments 10 to 15, wherein the composite particles have an average particle size of from about 40.0 µm to about 50.0 µm.

The composite particles of any one of embodiments 10 to 16, wherein the porous, inorganic particles comprise an agglomeration of newly exposed internal inorganic particle surfaces, and (ii) the at least one active ingredient is in contact with said newly exposed internal inorganic particle surfaces.

The composite particles of any one of embodiments 10 to 17, wherein the at least one active ingredient comprises newly exposed internal active ingredient surfaces, and the at least one active ingredient is in contact with the porous, inorganic particles via (i) the newly exposed internal inorganic particle surfaces, (ii) the newly exposed internal active ingredient surfaces, or (iii) both (i) and (ii).

Porous, Inorganic Particles and Composite Particles

The porous inorganic particles of any one of embodiments 1 to 8 or the composite particles of any one of embodiments 9 to 18, wherein the porous, inorganic particles have a mean pore diameter of about 1.0 nm to about 100.0 nm.

The porous inorganic particles of any one of embodiments 1 to 8 or the composite particles of any one of embodiments 9 to 19, wherein the porous, inorganic particles have a mean pore diameter of about 2.0 nm to about 50.0 nm.

The porous inorganic particles of any one of embodiments 1 to 8 or the composite particles of any one of embodiments 9 to 20, wherein the porous, inorganic particles have a BET particle surface area of at least about 100 $m^2/g$ up to 1500 $m^2/g$, or greater.

The porous inorganic particles of any one of embodiments 1 to 8 or the composite particles of any one of embodiments 9 to 21, wherein the porous, inorganic particles have a BET particle surface area of at least about 100 $m^2/g$ up to 500 $m^2/g$.

The porous inorganic particles of any one of embodiments 1 to 8 or the composite particles of any one of embodiments 9 to 22, wherein the porous, inorganic particles comprise inorganic oxide particles.

The porous inorganic particles of any one of embodiments 1 to 8 or the composite particles of any one of embodiments 9 to 23, wherein the porous, inorganic particles comprise metal oxide particles. In one embodiment, the metal oxide particles are mesoporous metal oxide particles.

The porous inorganic particles of any one of embodiments 1 to 8 or the composite particles of any one of embodiments 9 to 24, wherein the inorganic particles comprise silica particles.

The porous inorganic particles of any one of embodiments 1 to 8 or the composite particles of any one of embodiments 9 to 25, wherein the porous, inorganic particles comprise silica particles commercially available under the tradenames SYLOID® FP, AL1-FP, or silica particles commercially available under the tradename SYLOID® XDP, and in either case, the silica particles have been mechanically altered to provide newly exposed internal silica particle surfaces thereon.

The composite particles of any one of embodiments 9 to 26, wherein the at least one active ingredient comprises a particulate active ingredient.

The composite particles of any one of embodiments 9 to 27, wherein the at least one active ingredient comprises an active pharmaceutical ingredient (API), an agricultural chemical, a food additive, or any combination thereof.

The composite particles of any one of embodiments 9 to 28, wherein the at least one active ingredient comprises an active pharmaceutical ingredient (API) having an initial crystalline structure.

The composite particles of any one of embodiments 9 to 29, wherein the at least one active ingredient comprises an active pharmaceutical ingredient (API) selected from ibuprofen, ezetimibe, or any combination thereof.

The composite particles of any one of embodiments 9 to 30, wherein the (i) porous, inorganic particles and (ii) the at least one active ingredient are present at a weight ratio of porous, inorganic particles to the at least one active ingredient ranging from about 100:1 to 1:100.

The composite particles of any one of embodiments 9 to 31, wherein the (i) porous, inorganic particles and (ii) the at least one active ingredient are present at a weight ratio of porous, inorganic particles to the at least one active ingredient ranging from about 10:1 to 1:10.

The composite particles of any one of embodiments 9 to 32, wherein the (i) porous, inorganic particles and (ii) the at least one active ingredient are present at a weight ratio of porous, inorganic particles to the at least one active ingredient ranging from about 2:1 to 1:2.

The porous inorganic particles of any one of embodiments 1 to 8 or the composite particles of any one of embodiments 9 to 33, wherein said particles comprise less than about 5.0 wt % water based on a total weight of said particles.

The porous inorganic particles of any one of embodiments 1 to 8 or the composite particles of any one of embodiments 9 to 34, wherein said particles comprise less than about 1.0 wt % water based on a total weight of said particles.

The composite particles of any one of embodiments 9 to 35, wherein said composite particles consist essentially of said porous, inorganic particles, and said at least one active ingredient.

The composite particles of any one of embodiments 9 to 36, wherein said composite particles consist of said porous, inorganic particles, and said at least one active ingredient.

The porous inorganic particles of any one of embodiments 1 to 8 or the composite particles of any one of embodiments 9 to 37, wherein said porous inorganic particles are formed by mechanically altering, via a milling or extrusion step, porous inorganic particles having a total pore volume, of greater than 0.3, preferably greater than 1.0, cc/gm, as measured by mercury intrusion porosimetry (i.e. or any value greater than 0.3 cc/gm up to and including 15.0 cc/gm, preferably any value greater than 1.0 cc/gm up to and including 10.0, as determined by mercury intrusion porosimetry).

Methods of Making Porous Inorganic Particles

A method of preparing the porous inorganic particles of any one of embodiments 1 to 8, said method comprising: providing initial porous inorganic particles having a total pore volume, as measured by mercury intrusion porosimetry; and subjecting the particles in a dry, soventless environment to an amount of mechanical force sufficient to form newly exposed internal inorganic particle surfaces, and thereafter allowing consolidation or re-agglomeration of at least a portion of the particles to form porous inorganic particles having a total pore volume smaller than the total pore volume of the initial porous inorganic particles.

A method of preparing porous inorganic particles, said method comprising: providing porous inorganic particles having a total pore volume of greater than 1.0 cc/gm, as measured by mercury intrusion porosimetry (i.e., or any value greater than 1.0 cc/gm up to and including 10.0 cc/gm, in increments of 0.01 cc/gm, e.g., 6.00 cc/gm, or any range of values between greater than 1.0 cc/gm up to and including 10.0 cc/gm, in increments of 0.01 cc/gm, e.g., from about 1.01 cc/gm to about 9.99 cc/gm, as determined by mercury intrusion porosimetry); and subjecting the particles in a dry, soventless environment to mechanical force in an amount sufficient to form porous inorganic particles having a total pore volume of less than 1.0 cc/gm (or any value greater than 0 cc/gm up to and including 1.0 cc/gm, in increments of 0.01 cc/gm, e.g., 0.32 cc/gm, or any range of values between greater than 0 cc/gm up to and including 1.0 cc/gm, in increments of 0.01 cc/gm, e.g., from about 0.30 cc/gm to about 0.34 cc/gm), as determined by mercury intrusion porosimetry, and (ii) an intra-particle pore volume of less than 0.3 cc/gm (or any value greater than 0 cc/gm up to and including 0.3 cc/gm, in increments of 0.01 cc/gm, e.g., 0.09 cc/gm, or any range of values between greater than 0 cc/gm up to and including 0.3 cc/gm, in increments of 0.01 cc/gm, e.g., from about 0.09 cc/gm to about 0.11 cc/gm), as determined by mercury intrusion porosimetry, wherein the intra-particle pores are defined as pores having a pore size of less than or equal to 2200 Å.

The method of embodiment 40, wherein the particles have (i) a total pore volume of greater than 0 and less than about 0.98 cc/gm, as determined by mercury intrusion porosimetry, and (ii) an intra-particle pore volume of greater than 0 and less than about 0.28 cc/gm, as determined by mercury intrusion porosimetry.

The method of embodiment 40 or 41, wherein the particles have (i) a total pore volume of from about 0.15 to about 0.93 cc/gm, as determined by mercury intrusion porosimetry, and (ii) an intra-particle pore volume of from about 0.05 to about 0.24 cc/gm, as determined by mercury intrusion porosimetry.

The method of any one of embodiments 40 to 42, wherein the particles have (i) a total pore volume of from about 0.25 to about 0.40 cc/gm, as determined by mercury intrusion porosimetry, and (ii) an intra-particle pore volume of from about 0.08 to about 0.16 cc/gm, as determined by mercury intrusion porosimetry.

The method of any one of embodiments 40 to 43, wherein the particles have a final average particle size of from about 1.0 micron (μm) to about 100 μm (or any value between and including 1.0 μm to about 100 μm, in increments of 0.1 μm, e.g., 45.0 μm, or any range of values between and including 1.0 μm to about 100 μm, in increments of 0.1 μm, e.g., from about 3.2 μm to about 50.1 μm).

The method of any one of embodiments 40 to 44, wherein the particles have a final average particle size of from about 2.0 μm to about 60 μm.

The method of any one of embodiments 40 to 45, wherein the particles have a final average particle size of from about 40.0 μm to about 50.0 μm.

Methods of Making Composite Particles

A method of preparing the composite particles of any one of embodiments 9 to 38, said method comprising: providing initial porous inorganic particles having a total pore volume and at least one active ingredient; and subjecting the particles and the active ingredient in a dry, soventless environment to an amount of mechanical force sufficient to form composite inorganic particles having the active ingredient mechanically incorporated into pores thereof, wherein the composite inorganic particle have a total pore volume smaller than the total pore volume of the initial porous inorganic particles.

A method of making composite particles, said method comprising: providing initial porous inorganic particles having a total pore volume of greater than 1.0 cc/gm, as measured by mercury intrusion porosimetry (i.e., or any value greater than 1.0 cc/gm up to and including 10.0 cc/gm, in increments of 0.01 cc/gm, e.g., 6.00 cc/gm, or any range of values between greater than 1.0 cc/gm up to and including 10.0 cc/gm, in increments of 0.01 cc/gm, e.g., from about 1.01 cc/gm to about 9.99 cc/gm, as determined by mercury intrusion porosimetry) and a least one active ingredient; and subjecting the particles and active ingredient in a dry, soventless environment to mechanical force sufficient to form composite porous inorganic particles having the active ingredient mechanically incorporated into at least a portion of the pores of the composite particles, wherein the composite particles have a total pore volume to less than 1.0 cc/gm (or any value greater than 0 cc/gm up to and including 1.0 cc/gm, in increments of 0.01 cc/gm, e.g., 0.32 cc/gm, or any range of values between greater than 0 cc/gm up to and including 1.0 cc/gm, in increments of 0.01 cc/gm, e.g., from about 0.30 cc/gm to about 0.34 cc/gm), as determined by mercury intrusion porosimetry, and (ii) an intra-particle pore volume of less than 0.3 cc/gm (or any value greater than 0 cc/gm up to and including 0.3 cc/gm, in increments of 0.01 cc/gm, e.g., 0.09 cc/gm, or any range of values between greater than 0 cc/gm up to and including 0.3 cc/gm, in increments of 0.01 cc/gm, e.g., from about 0.09 cc/gm to about 0.11 cc/gm), as determined by mercury intrusion porosimetry, and wherein the intra-particle pores are defined as pores having a pore size of less than or equal to 2200 Å.

The method of embodiment 48, wherein the composite particles have (i) a total pore volume of greater than 0 and less than about 0.98 cc/gm, as determined by mercury intrusion porosimetry, and (ii) an intra-particle pore volume of greater than 0 and less than about 0.28 cc/gm, as determined by mercury intrusion porosimetry.

The method of embodiment 48 or 49, wherein the composite particles have (i) a total pore volume of from about 0.15 to about 0.93 cc/gm, as determined by mercury intrusion porosimetry, and (ii) an intra-particle pore volume of from about 0.05 to about 0.24 cc/gm, as determined by mercury intrusion porosimetry.

The method of any one of embodiments 48 to 50, wherein the composite particles have (i) a total pore volume of from about 0.25 to about 0.40 cc/gm, as determined by mercury intrusion porosimetry, and (ii) an intra-particle pore volume of from about 0.08 to about 0.16 cc/gm, as determined by mercury intrusion porosimetry.

The method of any one of embodiments 48 to 51, wherein the composite particles have a final average particle size of from about 1.0 μm to about 100 μm (or any value between and including 1.0 μm to about 100 μm, in increments of 0.1 μm, e.g., 45.0 μm, or any range of values between and including 1.0 μm to about 100 μm, in increments of 0.1 μm, e.g., from about 3.2 μm to about 50.1 μm).

The method of any one of embodiments 48 to 52, wherein the composite particles have a final average particle size of from about 2.0 μm to about 60 μm.

The method of any one of embodiments 48 to 53, wherein the composite particles have a final average particle size of from about 40.0 μm to about 50.0 μm.

Methods of Making Porous Inorganic Particles and Composite Particles

The method of any one of embodiments 47 to 54, wherein said subjecting step results in smaller active ingredient particles from the at least one active ingredient, the smaller active ingredient particles having newly exposed internal active ingredient surfaces, and the composite particles comprise (i) at least a portion of the smaller inorganic particles in contact with (ii) at least a portion of the smaller active ingredient particles via (i) the newly exposed internal inorganic particle surfaces, (ii) the newly exposed internal active ingredient surfaces, or (iii) both (i) and (ii).

The method of any one of embodiments 39 to 55, wherein the inorganic particles have a mean pore diameter of about 1.0 nm to about 100.0 nm.

The method of any one of embodiments 39 to 56, wherein the inorganic particles have a mean pore diameter of about 2.0 nm to about 50.0 nm.

The method of any one of embodiments 39 to 57, wherein the inorganic particles have a BET particle surface area of at least about 100 $m^2/g$ up to 1500 $m^2/g$, or greater.

The method of any one of embodiments 39 to 58, wherein the inorganic particles have a BET particle surface area of from about 100 $m^2/g$ to about 500 $m^2/g$.

The method of any one of embodiments 39 to 59, wherein the inorganic particles comprise metal particles.

The method of any one of embodiments 39 to 60, wherein the inorganic particles comprise mesoporous metal particles.

The method of any one of embodiments 39 to 61, wherein the inorganic particles comprise silica particles.

The method of any one of embodiments 39 to 62, wherein the inorganic particles comprise silica particles commercially available under the tradename SYLOID® 244FP or silica particles commercially available under the tradename SYLOID® XDP, and in either case, have been subjected to said decreasing step.

The method of any one of embodiments 47 to 63, wherein the at least one active ingredient comprises an active pharmaceutical ingredient (API), an agricultural chemicals, a food additive, or any combination thereof.

The method of any one of embodiments 47 to 64, wherein the at least one active ingredient comprises an active pharmaceutical ingredient (API) having a crystalline structure.

The method of any one of embodiments 47 to 65, wherein the at least one active ingredient comprises an active pharmaceutical ingredient (API) selected from ibuprofen, ezetimibe, or any combination thereof.

The method of any one of embodiments 47 to 66, wherein the (i) inorganic particles and (ii) the at least one active ingredient are present at a weight ratio of inorganic particles to the at least one active ingredient ranging from about 100:1 to 1:100.

The method of any one of embodiments 47 to 67, wherein the (i) inorganic particles and (ii) the at least one active ingredient are present at a weight ratio of inorganic particles to the at least one active ingredient ranging from about 10:1 to 1:10.

The method of any one of embodiments 47 to 68, wherein the (i) inorganic particles and (ii) the at least one active ingredient are present at a weight ratio of inorganic particles to the at least one active ingredient ranging from about 2:1 to 1:2.

The method of any one of embodiments 39 to 69, wherein said subjecting step comprises utilizing grinding balls, jetted fluid or at least one extruder screw to decrease the average particle size of the mixture of particles.

The method of any one of embodiments 39 to 70, wherein said subjecting step comprises utilizing grinding balls, jetted fluid or at least one extruder screw to cause re-agglomerization and formation of the particles.

The method of any one of embodiments 39 to 71, wherein said subjecting step comprises utilizing grinding balls to decrease the average particle size of the mixture of particles.

The method of any one of embodiments 39 to 72, wherein said subjecting step comprises utilizing grinding balls to cause re-agglomerization and formation of the particles.

The method of any one of embodiments 39 to 73, wherein said subjecting step occurs in a vibration ball mill comprising a milling chamber and grinding balls.

The method of embodiment 74, wherein the vibration ball mill operates at a frequency ranging from about 12 to about 90 Hertz (Hz) (or any value between 12 and 90 Hz, in increments of 1.0 Hz, e.g., 18 Hz, or any range of values between 12 and 90 Hz, in increments of 1.0 Hz, e.g., from about 18 Hz to about 28 Hz). Desirably, the vibration ball mill operates at a frequency that enables a crystalline active ingredient (e.g., a drug) to undergo amorphonization to an amorphous state when in composite particle form. In some desired embodiments, for example, this amorphonization-inducing frequency ranges from about 18 Hz to about 30 Hz depending on the active ingredient utilized. See, for example, Samples 5 and 11 in Examples 1-2 below, where a frequency of 20 Hz resulted in amorphonization of the crystalline drugs ibuprofen and ezetimibe into an amorphous state.

The method of embodiment 74 or 75, wherein the vibration ball mill is in operation for a milling time of less than about 25 minutes (or any value between greater than about 10 seconds, in increments of 1.0 second, e.g., 45 seconds, or any range of values between about 10 seconds and 25 minutes, in increments of 1.0 second, e.g., from about 60 seconds to about 5 minutes). Desirably, the vibration ball mill operates for a milling time (and frequency) that enables a crystalline active ingredient (e.g., a drug) to undergo amorphonization to an amorphous state when in composite particle form. In some desired embodiments, for example, this amorphonization-inducing milling time ranges from about 1.0 minute to about 20 minutes depending on the active ingredient utilized. See, for example, Samples 5 and 11 in Examples 1-2 below, where a milling time of 1.0 minute and 5 minutes, respectively, resulted in amorphonization of the crystalline drugs ibuprofen and ezetimibe into an amorphous state.

The method of any one of embodiments 39 to 76, wherein said subjecting step occurs in a vibration ball mill comprising a milling chamber and grinding balls, the vibration ball mill operating at a frequency ranging from about 20 to about 90 Hertz (Hz) with a milling time of less than about 25 minutes. In some desired embodiments, the vibration ball mill operates at a frequency ranging from about 20 to about 30 Hz with a milling time of from about 1.0 minute to about 5 minutes.

The method of any one of embodiments 39 to 77, wherein said subjecting step occurs in a vibration ball mill comprising a milling chamber and grinding balls, the vibration ball mill operating at a frequency ranging from about 20 to about 40 Hertz (Hz) with a milling time of less than about 90 seconds.

The method of any one of embodiments 39 to 78, wherein said subjecting step occurs in a vibration ball mill comprising a milling chamber and grinding balls, the vibration ball mill operating at a frequency ranging from about 20 to about 30 Hertz (Hz) with a milling time of less than about 60 seconds.

The method of any one of embodiments 47 to 79, wherein said method further comprises: introducing the inorganic particles and the at least one active ingredient into a vibration ball mill comprising a milling chamber and grinding balls, the vibration ball mill operating at a frequency ranging from about 20 to about 90 Hertz (Hz).

The method of any one of embodiments 70 to 80, wherein the (i) inorganic particles, (ii) at least one active ingredient, and (iii) grinding balls are present at a weight ratio of (i) to (ii) to (iii) ranging from about 1 to 100:1 to 100:1 to 100.

The method of any one of embodiments 70 to 81, wherein the (i) inorganic particles, (ii) at least one active ingredient, and (iii) grinding balls are present at a weight ratio of (i) to (ii) to (iii) ranging from about 1 to 10:1 to 10:1 to 10.

The method of any one of embodiments 39 to 69, wherein said subjecting step comprises utilizing jetted fluid to decrease the average particle size of the mixture of particles.

The method of any one of embodiments 39 to 69 and 83, wherein said subjecting step comprises utilizing jetted fluid to cause re-agglomerization and formation of the particles.

The method of any one of embodiments 39 to 69 and 83 to 84, wherein said subjecting step occurs in a jet milling device.

The method of any one of embodiments 39 to 69, wherein said subjecting step comprises utilizing at least one extruder screw to decrease the average particle size of the mixture of particles.

The method of any one of embodiments 39 to 69 and 86, wherein said subjecting step comprises utilizing at least one extruder screw to cause re-agglomerization and formation of the particles.

The method of any one of embodiments 39 to 69 and 86 to 87, wherein said subjecting step occurs in an extruder.

The method of any one of embodiments 47 to 88, wherein said method further comprises: drying (i) the inorganic particles, (ii) the at least one active ingredient, or (iii) both (i) and (ii) prior to said decreasing step.

The method of any one of embodiments 39 to 89, wherein the mixture of particles comprises less than about 5.0 wt % water based on a total weight of the mixture of particles.

The method of any one of embodiments 39 to 90, wherein the mixture of particles comprises less than about 1.0 wt % water based on a total weight of the mixture of particles.

The method of any one of embodiments 39 to 91, wherein said method reaches a particle equilibrium within less than about 10 minutes (or any time between greater than about 10 seconds and 10 minutes, in increments of 1.0 second), the particle equilibrium representing a point at which further processing does not result in larger particles. Desirably, the particle equilibrium also represents a point at which amorphonization of a crystalline active ingredient into an amorphous state in composite particle form takes place.

The method of any one of embodiments 39 to 92, wherein the particles resulting from said method have a final average particle size that is greater than the initial average particle size.

The method of any one of embodiments 39 to 93, wherein the particles have a final average particle size that is at least 1.0% greater than the initial average particle size.

The method of any one of embodiments 39 to 94, wherein the particles have a final average particle size that is from about 5.0 to about 25.0% greater than the initial average particle size.

The method of any one of embodiments 47 to 95, wherein the composite particles have a final average composite particle size that is at least 1.0% greater than an initial average particle size of either of (i) the inorganic particles or (ii) the at least one active ingredient.

The method of any one of embodiments 47 to 96, wherein the composite particles have a final average composite particle size that is from about 5.0 to about 25.0% greater than an initial average particle size of either of (i) the inorganic particles or (ii) the at least one active ingredient.

Porous, Inorganic Particles, Composite Particles and Pharmaceutical Compositions Porous, inorganic particles formed by the method of any one of embodiments 39 to 97.

Composite particles formed by the method of any one of embodiments 47 to 97.

A pharmaceutical composition comprising the composite particles of any one of embodiments 9 to 38.

The pharmaceutical composition of embodiment 100, in a form selected from a pill, a tablet, and a capsule.

Use of Porous, Inorganic Particles and Composite Particles

Use of the particles formed by the method of any one of embodiments 39 to 97 or the particles of any one of embodiments 1 to 38 and 98 to 99 or the pharmaceutical composition of embodiment 100 or 101 as an agent for delivering the at least one active ingredient into an environment.

Use of particles as an agent for delivering at least one active ingredient into an environment, the particles comprising porous inorganic particles having (i) a total pore volume of less than 1.0 cc/gm (or any value greater than 0 cc/gm up to and including 1.0 cc/gm, in increments of 0.01 cc/gm, e.g., 0.32 cc/gm, or any range of values between greater than 0 cc/gm up to and including 1.0 cc/gm, in increments of 0.01 cc/gm, e.g., from about 0.30 cc/gm to about 0.34 cc/gm), as determined by mercury intrusion porosimetry, and (ii) an intra-particle pore volume of less than 0.3 cc/gm (or any value greater than 0 cc/gm up to and including 0.3 cc/gm, in increments of 0.01 cc/gm, e.g., 0.09 cc/gm, or any range of values between greater than 0 cc/gm up to and including 0.3 cc/gm, in increments of 0.01 cc/gm, e.g., from about 0.09 cc/gm to about 0.11 cc/gm), as determined by mercury intrusion porosimetry, wherein the intra-particle pores are defined as pores having a pore size of less than or equal to 2200 Å.

Use of particles according to embodiment 103, wherein the particles have (i) a total pore volume of greater than 0 and less than about 0.98 cc/gm, as determined by mercury intrusion porosimetry, and (ii) an intra-particle pore volume of greater than 0 and less than about 0.28 cc/gm, as determined by mercury intrusion porosimetry.

Use of particles according to embodiment 103 or 104, wherein the particles have (i) a total pore volume of from about 0.15 to about 0.93 cc/gm, as determined by mercury intrusion porosimetry, and (ii) an intra-particle pore volume of from about 0.05 to about 0.24 cc/gm, as determined by mercury intrusion porosimetry.

Use of particles according to any one of embodiments 103 to 105, wherein the particles have (i) a total pore volume of from about 0.25 to about 0.40 cc/gm, as determined by mercury intrusion porosimetry, and (ii) an intra-particle pore volume of from about 0.08 to about 0.16 cc/gm, as determined by mercury intrusion porosimetry.

Use of particles according to any one of embodiments 103 to 106, wherein the particles have an average particle size of from about 1.0 μm to about 100 μm (or any value between and including 1.0 µm to about 100 µm, in increments of 0.1 µm, e.g., 45.0 µm, or any range of values between and including 1.0 µm to about 100 µm, in increments of 0.1 µm, e.g., from about 3.2 µm to about 50.1 µm).

Use of particles according to any one of embodiments 103 to 107, wherein the particles have an average particle size of from about 2.0 µm to about 60 µm.

Use of particles according to any one of embodiments 103 to 108, wherein the particles have an average particle size of from about 40.0 µm to about 50.0 µm.

Use of particles according to any one of embodiments 103 to 109, wherein the particles comprise mechanically altered inorganic particles having newly exposed internal inorganic particle surfaces thereon.

Use of composite particles as an agent for delivering at least one active ingredient into an environment, the composite particles comprising: (i) inorganic particles, and (ii) the at least one active ingredient mechanically incorporated in pores of the inorganic oxide particles, wherein the composite particles have (i) a total pore volume of less than 1.0 cc/gm (or any value greater than 0 cc/gm up to and including 1.0 cc/gm, in increments of 0.01 cc/gm, e.g., 0.32 cc/gm, or any range of values between greater than 0 cc/gm up to and including 1.0 cc/gm, in increments of 0.01 cc/gm, e.g., from about 0.30 cc/gm to about 0.34 cc/gm), as determined by mercury intrusion porosimetry, and (ii) an intra-particle pore volume of less than 0.3 cc/gm (or any value greater than 0 cc/gm up to and including 0.3 cc/gm, in increments of 0.01 cc/gm, e.g., 0.09 cc/gm, or any range of values between greater than 0 cc/gm up to and including 0.3 cc/gm, in increments of 0.01 cc/gm, e.g., from about 0.09 cc/gm to about 0.11 cc/gm), as determined by mercury intrusion porosimetry, wherein the intra-particle pores are defined as pores having a pore size of less than or equal to 2200 Å.

Use of the composite particles according to embodiment 111, wherein the composite particles have (i) a total pore volume of greater than 0 and less than about 0.98 cc/gm, as determined by mercury intrusion porosimetry, and (ii) an intra-particle pore volume of greater than 0 and less than about 0.28 cc/gm, as determined by mercury intrusion porosimetry.

Use of the composite particles according to embodiment 111 or 112, wherein the composite particles have (i) a total pore volume of from about 0.15 to about 0.93 cc/gm, as determined by mercury intrusion porosimetry, and (ii) an intra-particle pore volume of from about 0.05 to about 0.24 cc/gm, as determined by mercury intrusion porosimetry.

Use of the composite particles according to any one of embodiments 111 to 113, wherein the composite particles have (i) a total pore volume of from about 0.25 to about 0.40 cc/gm, as determined by mercury intrusion porosimetry, and (ii) an intra-particle pore volume of from about 0.08 to about 0.16 cc/gm, as determined by mercury intrusion porosimetry.

Use of the composite particles according to any one of embodiments 111 to 114, wherein the composite particles have an average particle size of from about 1.0 µm to about 100 µm (or any value between and including 1.0 µm to about 100 µm, in increments of 0.1 µm, e.g., 45.0 µm, or any range of values between and including 1.0 µm to about 100 µm, in increments of 0.1 µm, e.g., from about 3.2 µm to about 50.1 µm).

Use of the composite particles according to any one of embodiments 111 to 115, wherein the composite particles have an average particle size of from about 2.0 µm to about 60 µm.

Use of the composite particles according to any one of embodiments 111 to 116, wherein the composite particles have an average particle size of from about 40.0 µm to about 50.0 µm.

Use of the composite particles according to any one of embodiments 111 to 117, wherein the porous, inorganic oxide particles comprise newly exposed internal inorganic particle surfaces, and (ii) the at least one active ingredient is in contact with said newly exposed internal inorganic particle surfaces.

Use of the composite particles according to any one of embodiments 111 to 118, wherein the at least one active ingredient comprises newly exposed internal active ingredient surfaces, and the at least one active ingredient is in contact with the inorganic particles via (i) the newly exposed internal inorganic particle surfaces, (ii) the newly exposed internal active ingredient surfaces, or (iii) both (i) and (ii).

Use of the particles according to any one of embodiments 103 to 110 or the composite particles according to any one of embodiments 111 to 119, wherein the inorganic particles have a mean pore diameter of about 1.0 nm to about 100.0 nm.

Use of the particles according to any one of embodiments 103 to 110 or the composite particles according to any one of embodiments 111 to 120, wherein the inorganic particles have a mean pore diameter of about 2.0 nm to about 50.0 nm.

Use of the particles according to any one of embodiments 103 to 110 or the composite particles according to any one of embodiments 111 to 121, wherein the inorganic particles have a BET particle surface area of at least about 100 m$^2$/g up to 1500 m$^2$/g, or greater.

Use of the particles according to any one of embodiments 103 to 110 or the composite particles according to any one of embodiments 111 to 122, wherein the inorganic particles have a BET particle surface area of from about 100 m$^2$/g to about 400 m$^2$/g, or greater.

Use of the particles according to any one of embodiments 103 to 110 or the composite particles according to any one of embodiments 111 to 123, wherein the inorganic particles comprise inorganic oxide particles.

Use of the particles according to any one of embodiments 103 to 110 or the composite particles according to any one of embodiments 111 to 124, wherein the inorganic oxide particles comprise metal oxide particles. In one embodiment the metal oxide particles are mesoporous metal oxide particles.

Use of the particles according to any one of embodiments 103 to 110 or the composite particles according to any one of embodiments 111 to 125, wherein the inorganic particles comprise silica particles.

Use of the particles according to any one of embodiments 103 to 110 or the composite particles according to any one of embodiments 111 to 126, wherein the inorganic particles comprise silica particles commercially available under the tradename SYLOID® 244FP or silica particles commercially available under the tradename SYLOID® XDP, that, in either case, have been prepared via the method of any one of embodiments 39 to 97.

Use of the composite particles according to any one of embodiments 111 to 127, wherein the (i) inorganic particles and (ii) the at least one active ingredient are present at a weight ratio of inorganic particles to the at least one active ingredient ranging from about 100:1 to 1:100.

Use of the composite particles according to any one of embodiments 111 to 128, wherein the (i) inorganic particles and (ii) the at least one active ingredient are present at a weight ratio of inorganic particles to the at least one active ingredient ranging from about 10:1 to 1:10.

Use of the composite particles according to any one of embodiments 111 to 129, wherein the (i) inorganic particles and (ii) the at least one active ingredient are present at a weight ratio of inorganic particles to the at least one active ingredient ranging from about 2:1 to 1:2.

Use of the composite particles according to any one of embodiments 111 to 130, wherein the composite particles comprise less than about 5.0 wt % water based on a total weight of the composite particles.

Use of the composite particles according to any one of embodiments 111 to 131, wherein the composite particles comprise less than about 1.0 wt % water based on a total weight of the composite particles.

Use of the composite particles according to any one of embodiments 111 to 132, wherein the composite particles consist essentially of the inorganic particles, and the at least one active ingredient.

Use of the composite particles according to any one of embodiments 111 to 133, wherein the composite particles consist of the inorganic particles, and the at least one active ingredient.

Use of the composite particles according to any one of embodiments 111 to 134, wherein the at least one active ingredient comprise an active pharmaceutical ingredient (API).

Use of the composite particles according to any one of embodiments 111 to 135, wherein the at least one active ingredient comprise an active pharmaceutical ingredient (API) having an initial crystalline structure.

Use of the composite particles according to any one of embodiments 111 to 136, wherein the at least one active ingredient comprises an active pharmaceutical ingredient (API) selected from ibuprofen, ezetimibe, or any combination thereof.

Use of the particles according to any one of embodiments 103 to 110 or the composite particles according to any one of embodiments 111 to 133 as a dental or oral care product.

Use of the particles according to any one of embodiments 103 to 110 or the composite particles according to any one of embodiments 111 to 133 as a skin care product.

Use of the particles according to any one of embodiments 103 to 110 or the composite particles according to any one of embodiments 111 to 133 as a cosmetic product.

Use of the particles according to any one of embodiments 103 to 110 or the composite particles according to any one of embodiments 111 to 133 as a nutrition-providing product.

Use of the composite particles according to any one of embodiments 102 to 141, wherein the environment comprises a patient.

Use of the composite particles according to any one of embodiments 102 to 142, wherein the environment comprises an intestinal track of a patient.

Use of the composite particles according to any one of embodiments 111 to 133, wherein the at least one active ingredient comprises a plant nutrient or pesticide.

Use of the composite particles according to any one of embodiments 102 to 133 and 144, wherein the environment comprises a plant or in a vicinity of a plant.

Use of the particles according to any one of embodiments 103 to 110 or the composite particles according to any one of embodiments 111 to 133 in a catalytic application.

Use of the particles according to any one of embodiments 102 to 110 or the composite particles according to any one of embodiments 111 to 133 and 146, wherein the environment comprises a process reactor.

Use of the particles according to any one of embodiments 102 to 147, wherein the environment comprises an aqueous environment.

Use of the composite particles according to any one of embodiments 111 to 148, wherein the composite particles enable dissolution of at least 50 wt % of the at least one active ingredient into the environment within 20 minutes.

Use of the composite particles according to any one of embodiments 111 to 149, wherein the composite particles enable dissolution of at least 50 wt % of the at least one active ingredient into the environment within 5 minutes.

It should be understood that although the above-described porous, inorganic particles, composite particles, methods and uses are described as "comprising" one or more components or steps, the above-described porous, inorganic particles, composite particles, methods and uses may "comprise," "consists of," or "consist essentially of" any of the above-described components or steps of the porous, inorganic particles, composite particles, methods and uses. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a porous, inorganic particle, composite particle, method and/or use that "comprises" a list of elements (e.g., components or steps) is not necessarily limited to only those elements (or components or steps), but may include other elements (or components or steps) not expressly listed or inherent to the porous, inorganic particle, composite particle, method and/or use.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define porous, inorganic particles, composite particles, methods and/or uses that include materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Further, it should be understood that the herein-described porous, inorganic particles, composite particles, methods and/or uses may comprise, consist essentially of, or consist of any of the herein-described components and features, as shown in the figures with or without any feature(s) not shown in the figures. In other words, in some embodiments, the porous, inorganic particles, composite particles, methods and/or uses of the present invention do not have any additional features other than those shown in the figures, and such additional features, not shown in the figures, are specifically excluded from the porous, inorganic particles, composite particles, methods and/or uses. In other embodiments, the porous, inorganic particles, composite particles, methods and/or uses of the present invention do have one or more additional features that are not shown in the figures.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

The following examples describe (i) processes in accordance with the present invention for preparing porous, inorganic particles and composite particles, and (ii) the evaluation of the porous, inorganic particles and composite particles in drug dissolution processes.

In the Examples, the following grades of silica shown in Table 1 were utilized.

TABLE 1

Silicas Used In Examples

| Grade Name | Median Particle Size (μm) | BET Surface Area (m²/g) | Pore Volume (cc/g) |
|---|---|---|---|
| SYLOID ® 244FP | 5.5 | 300 | 1.5 |
| SYLOID ® XDP 3050 | 50 | 285 | 1.8 |
| SYLOID ® AL1-FP | 6.0 | 700 | 0.4 |

For the silicas shown in Table 1, median particle sizes were determined by laser light scattering (per ASTM B822-10) using a Malvern MASTERSIZER™ 2000, available from Malvern Instrument Ltd. Particle size is defined as median particle size by volume distribution. BET surface areas were obtained from nitrogen sorption analysis described in the literature. Median pore diameter, pore volume and pore size distribution were calculated based on mercury intrusion into 35-10000 Å size pores. Pore volume is defined as cumulative pore volume in the same pore size range, and median pore size is determined a pore diameter (size) at which 50% pore volume is contributed from smaller pores and 50% pore volume is contributed from bigger pores.

FIG. 1 graphically shows the surface groups of silica particles (such as the SYLOID® 244FP and SYLOID® XDP3050 silica used in the present examples) for active ingredient to have interactions with).

Figure 2A:
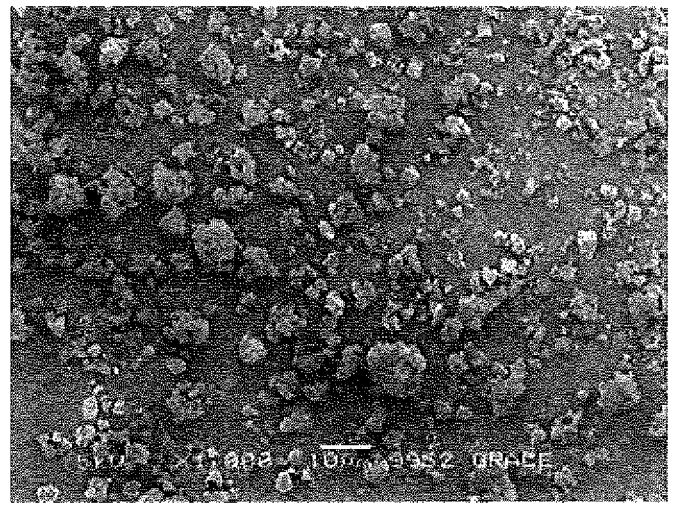
FIGS. 2A-2D depict (i) photographs of SYLOID® 244FP silica (at a magnification of 1000) prior to milling (i.e., FIG. 2A, upper left-hand photograph) and after milling (i.e., FIG. 2B, upper right-hand photograph), and (ii) graphs showing the cumulative pore volume of SYLOID® 244FP silica prior to milling (i.e., FIG. 2C, lower left-hand graph) and after milling (i.e., FIG. 2D, lower right-hand graph), as measured by mercury intrusion method.
Figure 2B:
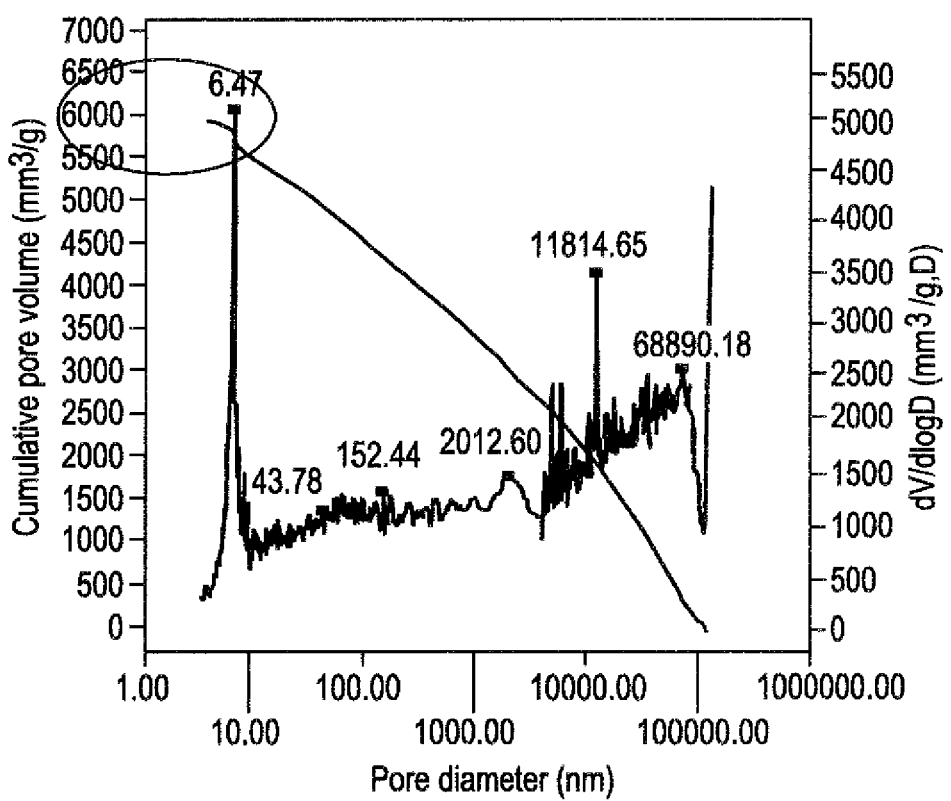
Figure 2C:
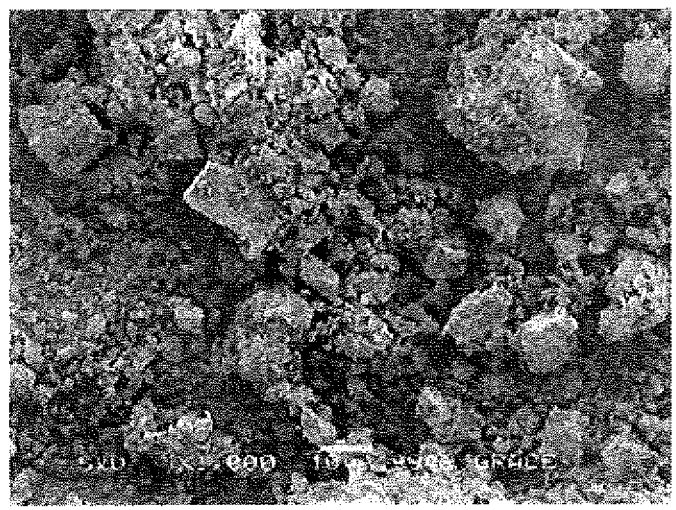
Figure 2D:
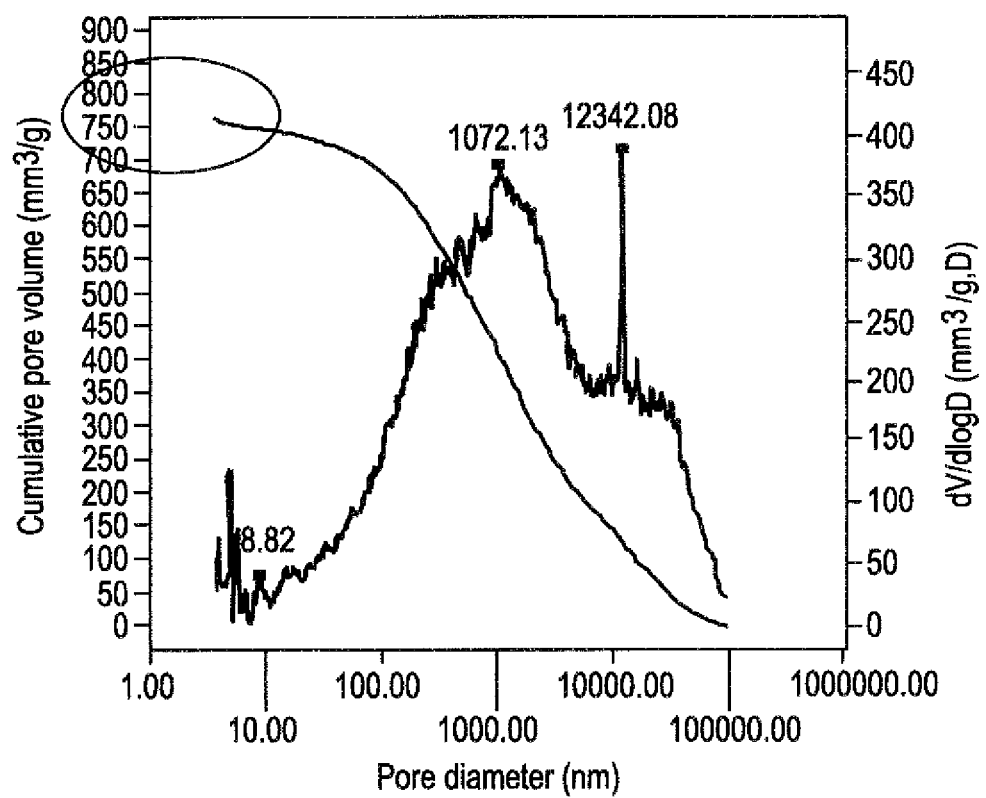

FIGS. 2A-2D demonstrate the changes in SYLOID® 244FP silica as a result of milling (i.e., using the exemplary vibration ball mill described in Example 1 below). FIG. 2A (i.e., upper left-hand photograph) depicts a photograph of SYLOID® 244FP silica prior to milling. FIG. 2B (i.e., upper right-hand photograph) depicts a photograph of SYLOID® 244FP silica after milling. As shown in FIGS. 2C-2D, the process of milling dramatically decreases the cumulative pore volume of SYLOID® 244FP silica. See, FIG. 2C (i.e., lower left-hand photograph) for the cumulative pore volume of SYLOID® 244FP silica prior to milling, and FIG. 2D (i.e., lower right-hand photograph) for the cumulative pore volume of SYLOID® 244FP silica after milling, as measured by mercury intrusion method.

Figure 3A:
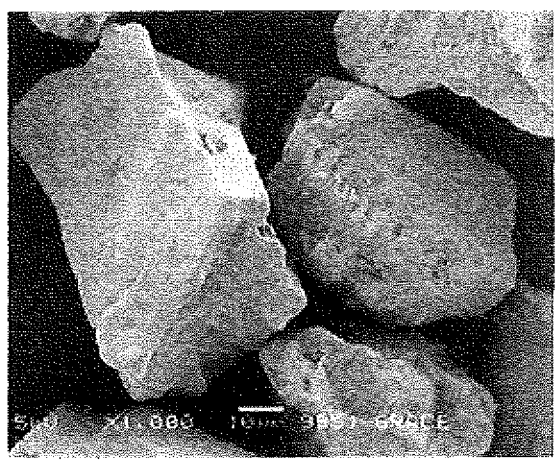
FIGS. 3A-3D depict (i) photographs of SYLOID® XDP3050 silica (at a magnification of 1000) prior to milling (i.e., FIG. 3A, upper left-hand photograph) and after milling (i.e., FIG. 3B, upper right-hand photograph), and (ii) graphs showing the cumulative pore volume of SYLOID® XDP3050 silica prior to milling (i.e., FIG. 3C, lower left-hand graph) and after milling (i.e., FIG. 3D, lower right-hand graph), as measured by mercury intrusion method.
Figure 3B:
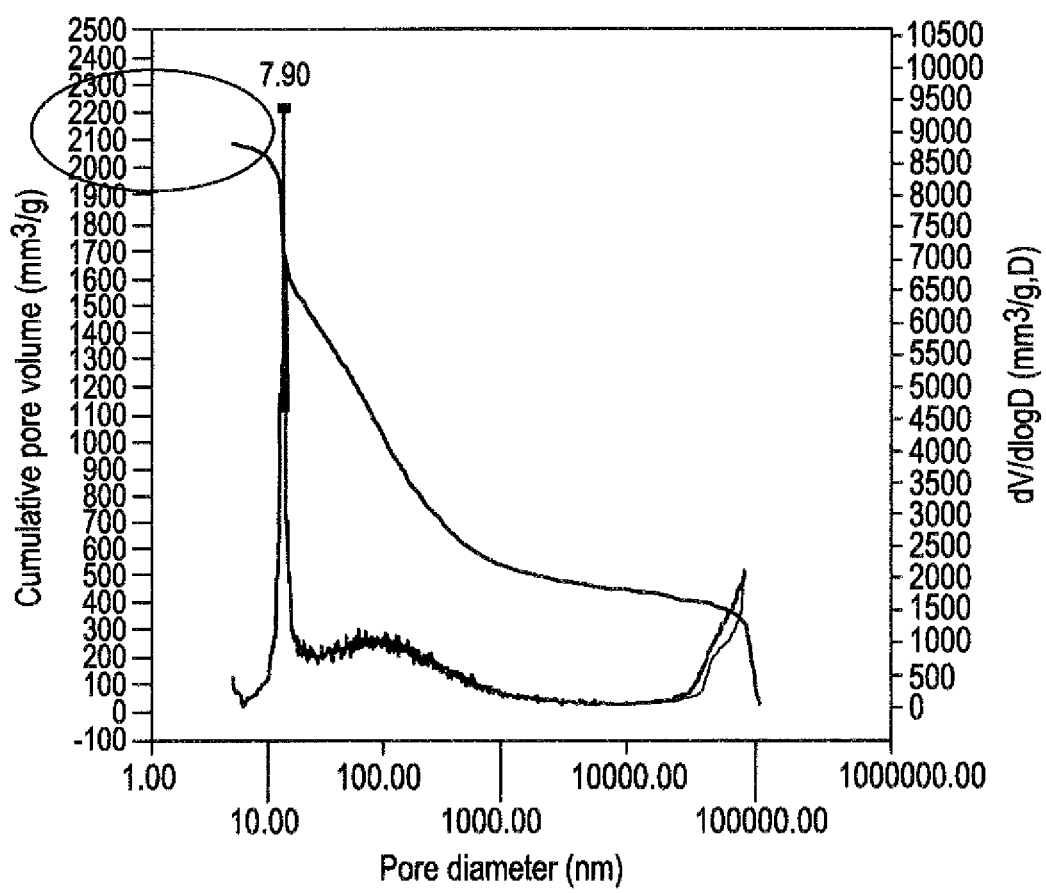
Figure 3C:
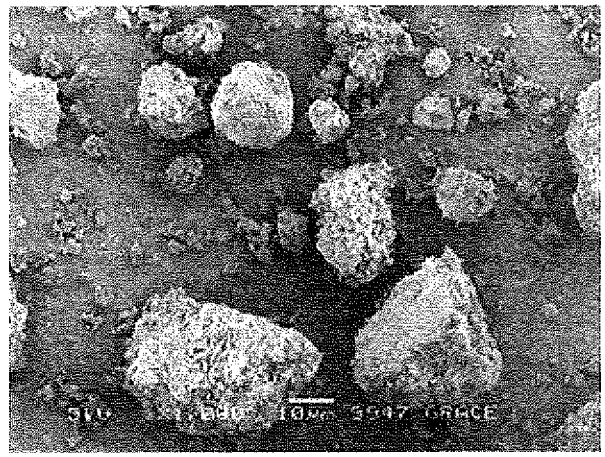
Figure 3D:
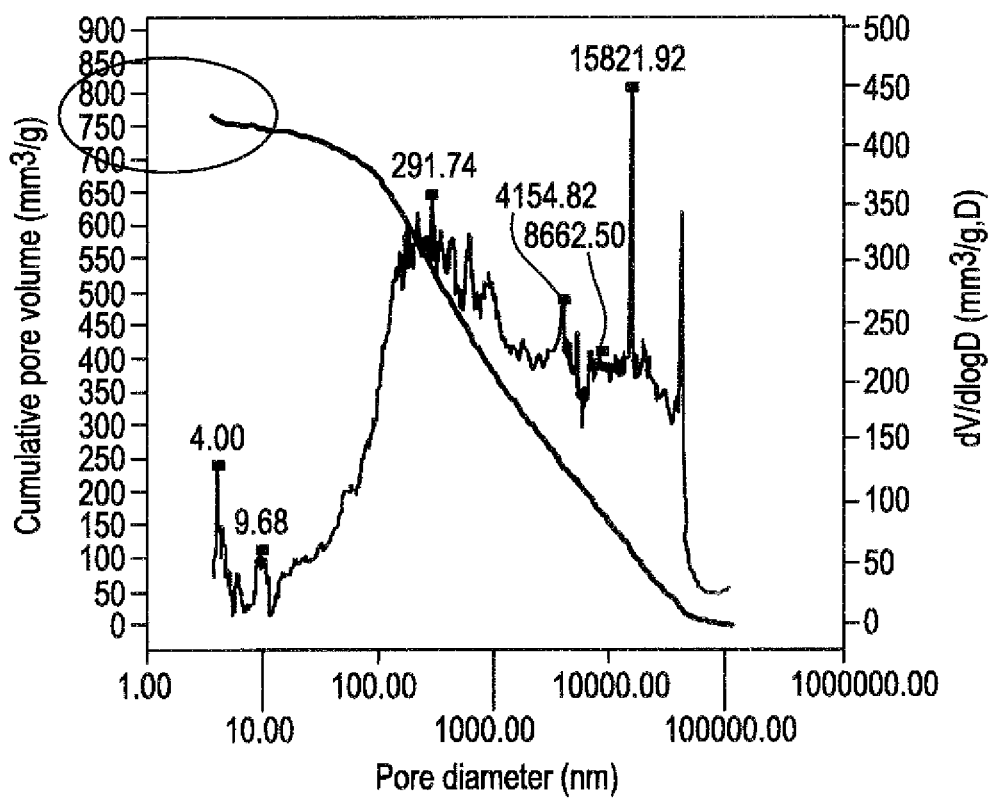

A similar result is demonstrated in FIGS. 3A-3D. FIGS. 3A-3D demonstrate the changes in SYLOID® XDP3050 silica as a result of milling. FIG. 3A (i.e., upper left-hand photograph) depicts a photograph of SYLOID® XDP3050 silica prior to milling. FIG. 3B (i.e., upper right-hand photograph) depicts a photograph of SYLOID® XDP3050 silica after milling. As shown in FIGS. 3C-3D, the process of milling dramatically decreases the cumulative pore volume of SYLOID® XDP3050 silica. See, FIG. 3C (i.e., lower left-hand photograph) for the cumulative pore volume of SYLOID® XDP3050 silica prior to milling, and FIG. 3D (i.e., lower right-hand photograph) for the cumulative pore volume of SYLOID® XDP3050 silica after milling, as measured by mercury intrusion method.

Example 1: Formation of Composite Particles Comprising Silica and Ibuprofen (IBU)

Composite particles were prepared by introducing the following amounts of silica particles and ibuprofen (IBU), as shown in Table 2 below, into a vibration ball mill, Mixer Mill MM400 commercially available from Retsch GmbH & Co. (Haan, Germany). The vibration ball mill consisted of (i) a stainless steel milling chamber having a chamber volume of 25 milliliters (ml), and two (2) stainless steel balls, each weighing 7.0 grams (g) and having a diameter of 12 millimeters (mm).

Silica samples were used as provided. Each silica sample was added to the vibration chamber.

Ibuprofen having an initial median particle size of about 2-3 mm was added to the vibration chamber.

The vibration mill was set at a given frequency and run for a milling time as shown in Table 3 below.

TABLE 2

Composite Particle Compositions

| Material | C1 | 1 | 2 | C2 | 3 | 4 | C3 | 5 | C4 | C5 | 6 | 7 | C6 | C7 |
|---|---|---|---|---|---|---|---|---|---|---|---|---|---|---|
| | | | | | | | Amount (mg) | | | | | | | |
| SYLOID ® 244FP silica | | 250 | | | | | | | | | | | | |
| SYLOID ® XDP 3050 silica | 250 | | 250 | 250 | 250 | | 417 | | | | 375 | 375 | | |

TABLE 2-continued

Composite Particle Compositions

| | Sample | | | | | | | | | | | | | |
|---|---|---|---|---|---|---|---|---|---|---|---|---|---|---|
| Material | C1 | 1 | 2 | C2 | 3 | 4 | C3 | 5 | C4 | C5 | 6 | 7 | C6 | C7 |
| | | | | | | | Amount (mg) | | | | | | | |
| ibuprofen | 500 | 250 | 250 | 250 | 250 | 250 | 500 | 83 | 500 | 500 | 125 | 125 | 250 | 250 |
| PVPK30 | | | | | | | | | | | | | 250 | |
| dextrose | | | | | | | | | | | | | | 250 |

TABLE 3

Process Parameters

| | Sample | | | | | | | | | | | | | |
|---|---|---|---|---|---|---|---|---|---|---|---|---|---|---|
| Parameter | C1 | 1 | 2 | C2 | 3 | 4 | C3 | 5 | C4 | C5 | 6 | 7 | C6 | C7 |
| frequency (Hz) | | | | | | | | 20 | 20 | 20 | 30 | 20 | | |
| milling time (minutes) | 15 | 15 | 15 | 0 | 5 | 25 | 0 | 1 | 1 | 40 | 60 | 40 | | |

Figure 10:
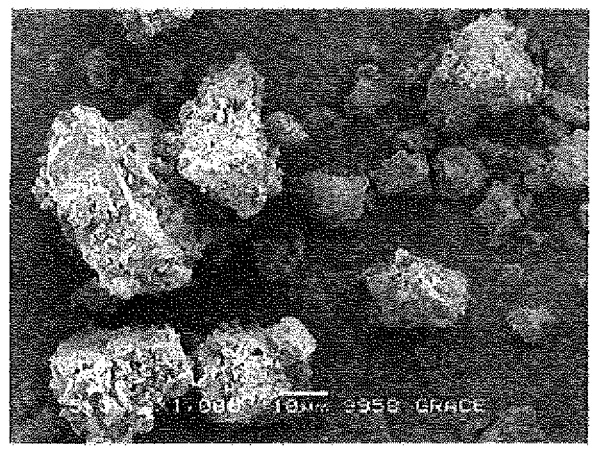
FIGS. 10-11 depict photographs of composite particles (at a magnification of 1000) similar to those formed in Example 1, namely, composite particles comprising (1) SYLOID® 244FP silica and ibuprofen (FIG. 7) and (2) SYLOID® XDP 3050 silica and ibuprofen (FIG. 8)
Figure 11:
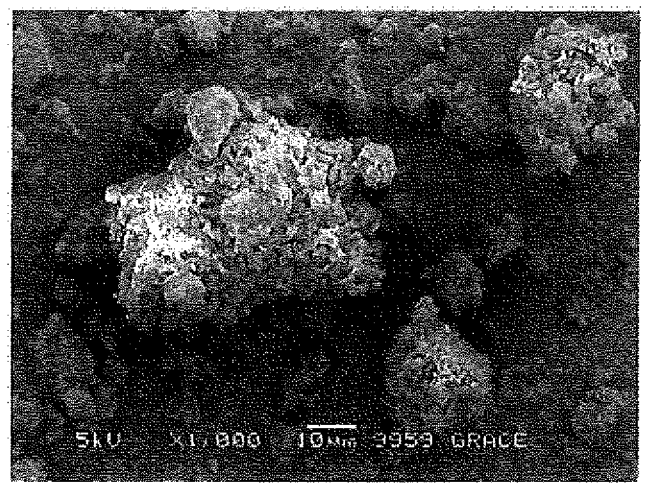

After co-milling, each sample was removed from the vibration chamber and analyzed. FIGS. 10 and 11 depict photographs of composite particles (at a magnification of 1000) similar to those formed in Example 1, namely, composite particles comprising (1) SYLOID® 244FP silica and ibuprofen (FIG. 10) and (2) SYLOID® XDP 3050 silica and ibuprofen (FIG. 11).

Numerous trials were conducted with various milling time varying from 1 minute (min) to 25 min. Further, the co-milled composite particles were compressed into tablet dosage form with other tableting aids (e.g., polyethylene glycol (PEG), sodium lauryl sulfate (SLS), etc.).

Amorphonisation of co-milled IBU was confirmed by DSC and X-RD study. Drug release studies were conducted by and using USP Dissolution apparatus I1 and media (e.g., acetate buffer) of pH 4.5.

Formation of hydrogen bond between silanol groups of SYLOID® silica and functional groups of IBU were believe to be the key to drug amorphonisation in the co-milling process. To confirm the IBU amorphonisation, X-ray diffraction study (XRD) was conducted. As shown in FIG. 4, both SYLOID® XDP 3050 silica and SYLOID® 244FP silica helped to decrease crystallinity of IBU by co-milling process. However, milled IBU alone does not result in an amorphous form. This showed the role of SYLOID® silica in crystalline drug amorphonisation into an amorphous state by co-milling process.

Figure 5A:
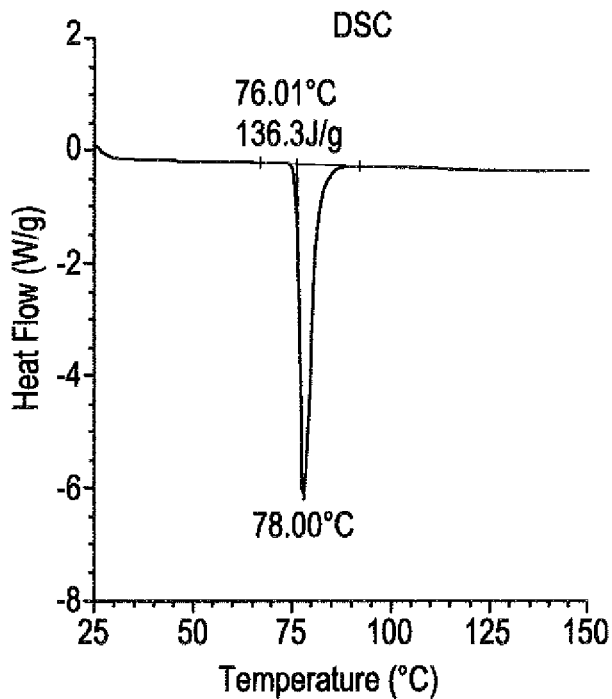
FIGS. 5A-5B graphically show DSC thermograms of ibuprofen milled alone versus ibuprofen co-milled with SYLOID® XDP silica as described in Example 1 below.
Figure 5B:
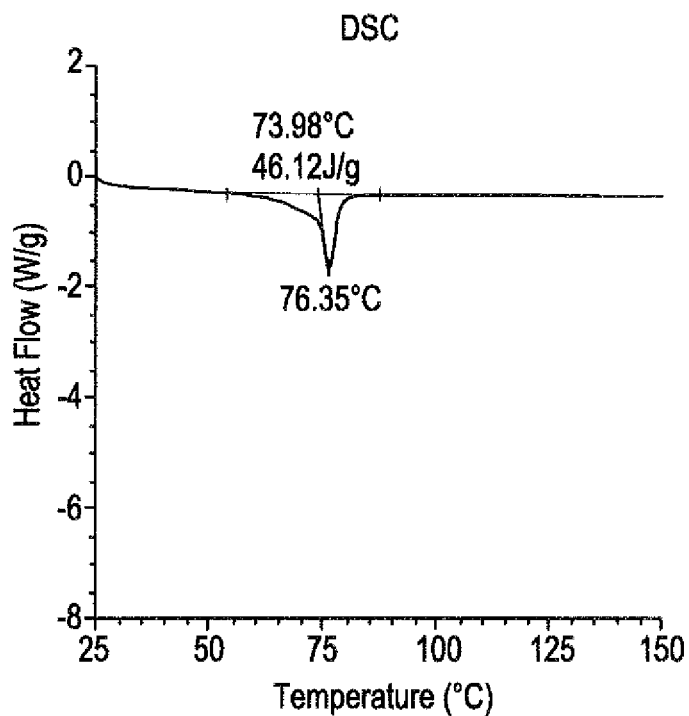

Additionally, DSC studies were conducted to understand the amorphonisation and possible interaction between silanol groups of SYLOID® silica and IBU. DSC thermograms, shown in FIGS. 5A-5B, confirmed both change in enthalpy and symmetry of peak shape. The variation in peak symmetry strongly suggested the interaction of silanol group with IBU. Change in enthalpy values also suggested that the IBU was getting converted to an amorphous form from a crystalline structure.

Figure 6:
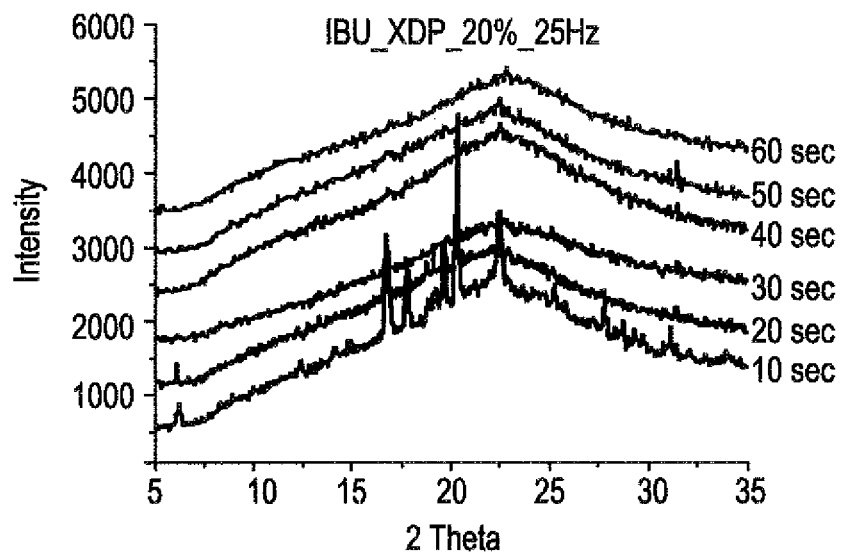
FIG. 6 graphically shows X-ray diffraction data for combinations of ibuprofen co-milled with SYLOID® XDP silica at various milling times.

Further, as shown in FIG. 6, X-ray diffraction data for combinations of ibuprofen co-milled with SYLOID® XDP 3050 silica at various milling times indicated conversion of the composite particle component combinations from a crystalline state (i.e., as indicated by sharp peaks along a given plot, e.g., the plot corresponding to the 10 second trial) to an amorphous state (i.e., as indicated by a smoother plot with less sharp peaks along a given plot, e.g., the plot corresponding to the 60 second trial).

Figure 7:
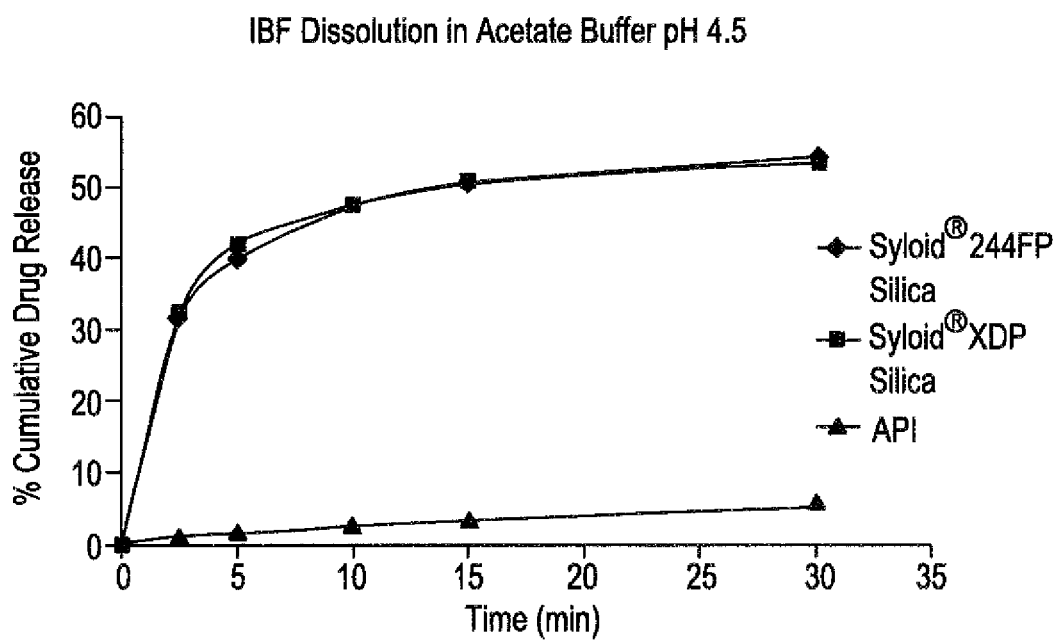
FIG. 7 graphically shows the dissolution of (i) ibuprofen milled alone versus (ii) ibuprofen co-milled with SYLOID® XDP silica and (iii) ibuprofen co-milled with SYLOID® XDP silica as described in Example 1 below.
Figure 9:
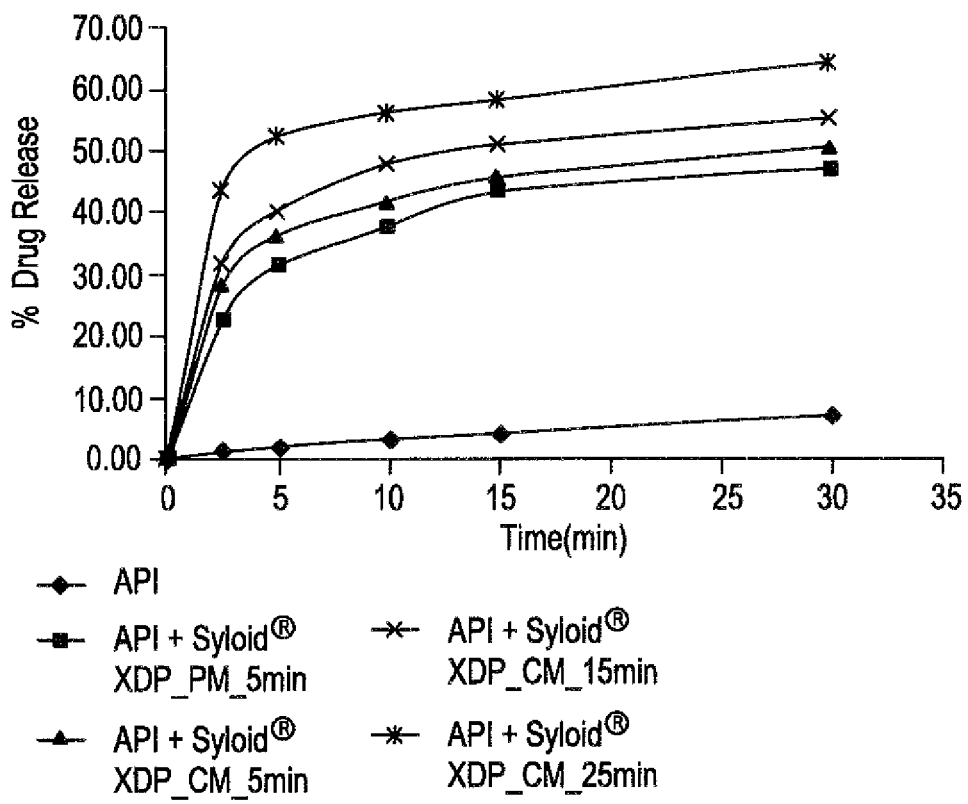
FIG. 9 graphically shows the effect of milling time on tablet dissolution of composite particles comprising ibuprofen co-milled with SYLOID® XDP 3050 silica using the procedure as described in Example 1.

Dissolution of co-milled samples SYLOID® XDP 3050+IBU and SYLOID® 244FP silicas+IBU were conducted in pH 4.5 buffer and compared with dissolution of alone milled IBU as shown in FIG. 7. The effect of milling time on the dissolution of co-milled samples of SYLOID® XDP 3050+IBU and SYLOID® 244FP silicas+IBU was determined in a pH 4.5 buffer and was again compared with dissolution of alone milled IBU as shown in FIG. 9. The obtained results showed significant improvement in dissolution of co-milled samples compared to IBU milled alone. The improved change in dissolution was believe due to the amorphous form of IBU formed during the co-milling process. This suggests that bioavailability of crystalline drugs can be improved using this process.

Figure 8:
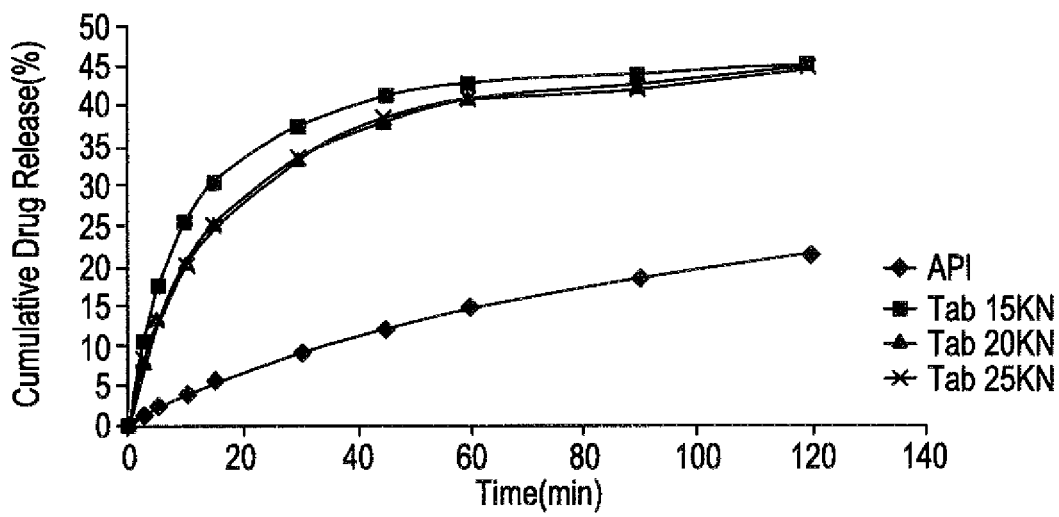
FIG. 8 graphically shows the effect of compression force on tablet dissolution of tablets comprising composite particles of Example 1, namely, composite particles comprising ibuprofen co-milled with SYLOID® XDP silica.

It was further observed that hydrogen bonding between SYLOID® silica and IBU remained unchanged at various compression forces from 15 KN to 25 KN as shown by the dissolution profile of tablets compressed at these forces in FIG. 8.

Figure 12:
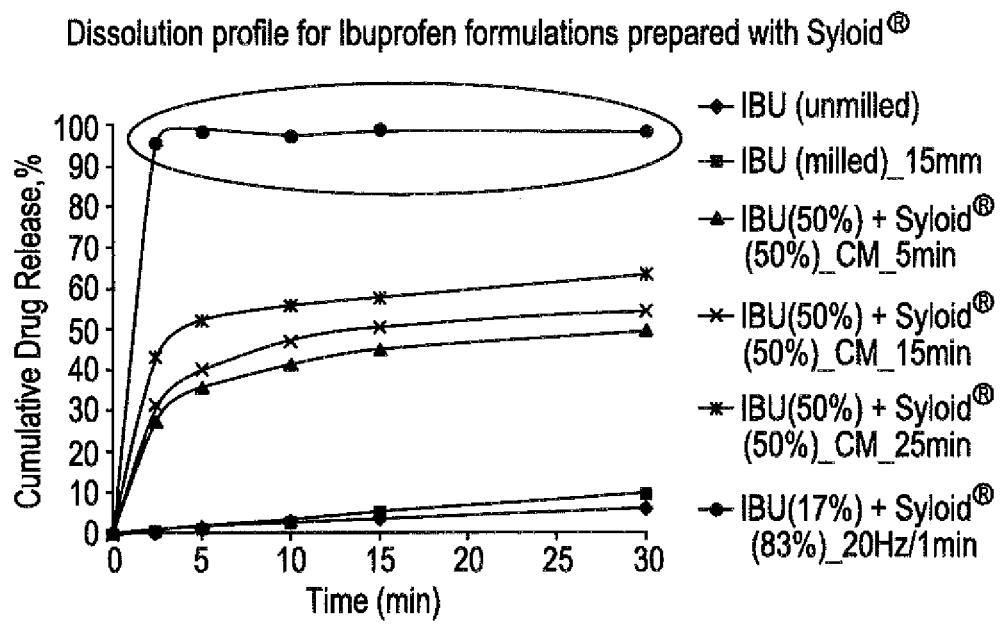
FIG. 12 graphically shows the effect of milling time on tablet dissolution of composite particles comprising ibuprofen co-milled with SYLOID® XDP silica at a 1:1 weight ratio or a 1:5 weight ratio using a procedure as outlined in Example 1.

FIG. 12 graphically shows the effect of milling time on tablet dissolution of composite particles comprising ibuprofen co-milled with SYLOID® XDP 3050 silica at a 1:1 weight ratio or a 1:5 weight ratio using the procedure as outlined in Example 1. Samples C3 (unmilled IBU), C1 (milled IBU alone), 3 (co-milled 5 min), 1 (co-milled 15 min), 4 (co-milled 25 min) and 5 (co-milled 1 min) were prepared as discussed above. As shown in FIG. 12, Sample 5 (co-milled 1 min at 20 Hz) provided exceptional drug dissolution compared to the other samples.

Figure 13:
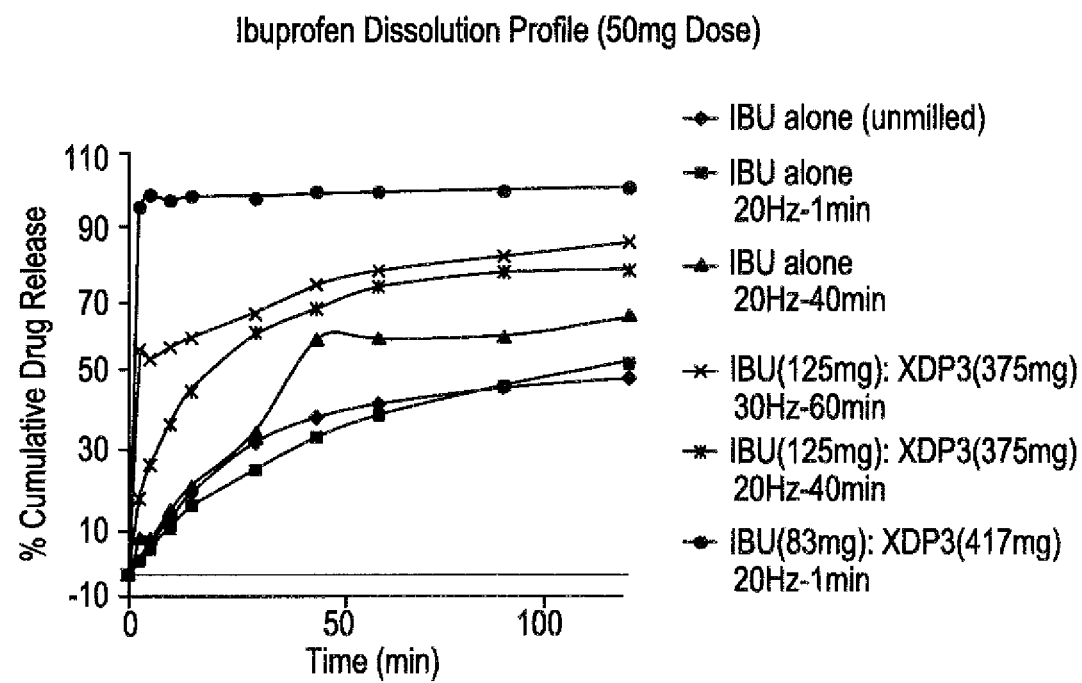
FIG. 13 graphically shows the effect of milling time on tablet dissolution of composite particles comprising ibuprofen co-milled with SYLOID® XDP silica at various weight ratios using a procedure as outlined in Example 1.

FIG. 13 graphically shows the effect of milling time on tablet dissolution of composite particles comprising ibuprofen co-milled with SYLOID® XDP 3050 silica at various weight ratios using the procedure as outlined in Example 1 above. Samples C3 (unmilled IBU), C4 (milled IBU 1 min), C5 (milled IBU 40 min), 6 (co-milled 60 min), 7 (co-milled 40 min), and 5 (co-milled 1 min) were prepared as discussed above. As shown in FIG. 13, Sample 5 (co-milled 1 min at 20 Hz) provided exceptional drug dissolution compared to the other samples.

Figure 14:
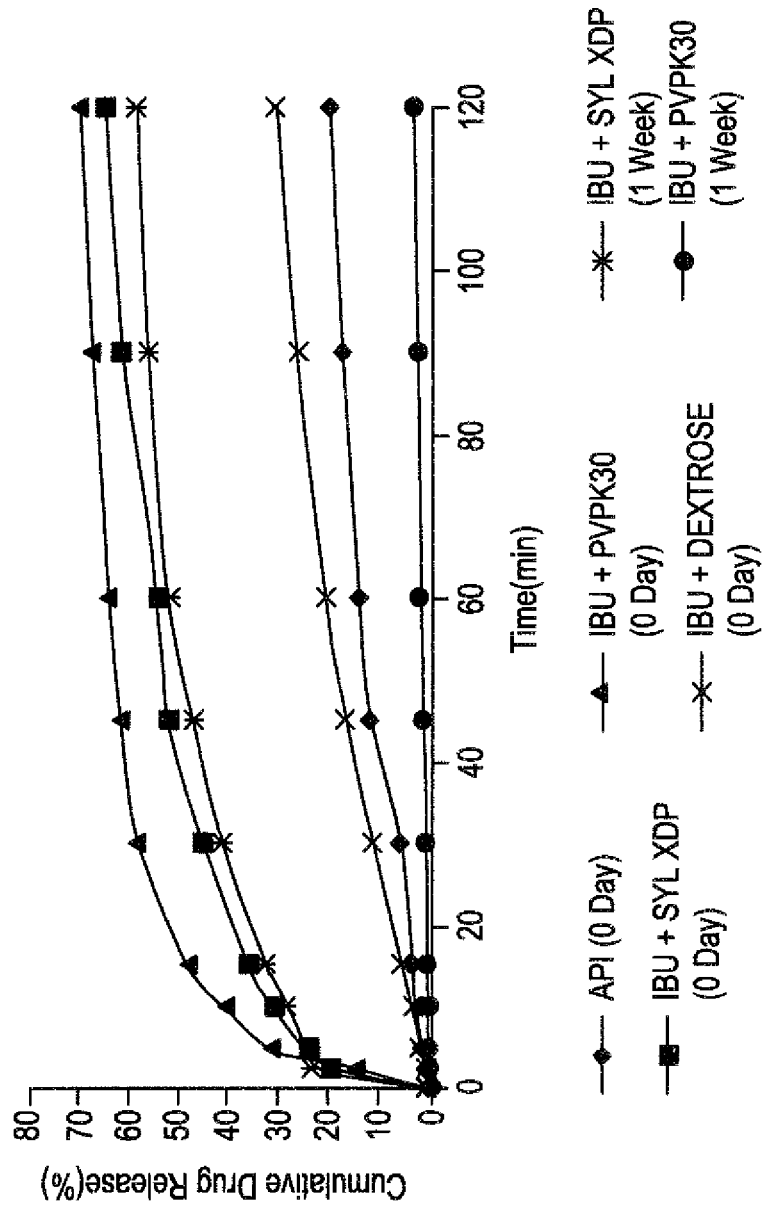
FIG. 14 graphically shows the effect of a given carrier and storage on tablet dissolution of composite particles comprising ibuprofen co-milled with various carriers using a procedure similar to that as outlined in Example 1.

FIG. 14 graphically shows the effect of a given carrier and storage time on tablet dissolution of composite particles comprising ibuprofen co-milled with various carriers using a procedure similar to that as outlined in Example 1 above. As shown in FIG. 14, samples comprising SYLOID® XDP silica as the carrier (i.e., composite particles comprising SYLOID® XDP silica in combination with ibuprofen) provided exceptional drug dissolution properties even after one week of storage time compared to the other samples. Although PVPK30-ibuprofen composite particles provided good drug dissolution properties initially, the drug dissolution properties decreased significantly after one week of storage.

In summary, in this example, from obtained observations of XRD and DSC, it was confirmed that drugs started converting from a crystalline to an amorphous form by co-milling with SYLOID® silica. Highly crowded silanol groups of SYLOID® silica interact with crystalline drug with mechanical force to form an amorphous form. This interaction was confirmed with DSC thermograms (FIGS. 5A-5B) and X-ray diffraction data (FIG. 6). The dissolution of alone milled drug did not show any improvement over un-milled drug; however, co-milled IBU with SYLOID® silica showed significant improvement in dissolution. This confirmed that co-milling of crystalline drug with SYLOID® silica helped to generate a stable amorphous form, which can help to increase bioavailability of drug. This method did not involve solvent or any special equipment and hence sounds to be industrially feasible, cost effective and time saving method of increasing oral bioavailability of crystalline & poorly water soluble drugs.

Example 2: Formation of Composite Particles Comprising Silica and Ezetimibe

Composite particles were prepared using the procedure and materials described in Example 1 above except ezetimibe was utilized instead of ibuprofen (IBU). Composite particle composition components were used as shown in Table 4 below.

Ezetimibe having an initial median particle size of about 2-3 mm was added to the vibration chamber.

The vibration mill was set at a given frequency and run for a milling time as shown in Table 5 below.

TABLE 5

Process Parameters

| Parameter | Sample | | | | | | | | |
|---|---|---|---|---|---|---|---|---|---|
| | C8 | 8 | 9 | C9 | C10 | 11 | 12 | 13 | C11 |
| frequency (Hz) | | | | | | 20 | 20 | 20 | — |
| milling time (minutes) | | 15 | — | 5 | 20 | 50 | 15 |

Figure 15:
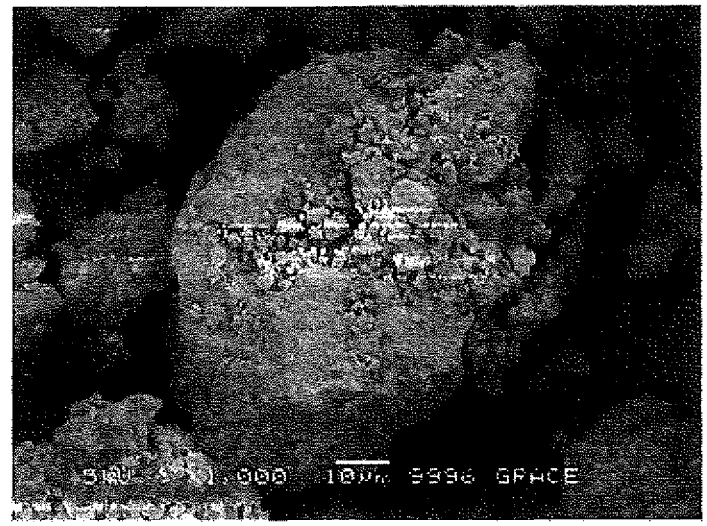
FIGS. 15-16 depict photographs of composite particles (at a magnification of 1000) formed in Example 2, namely, composite particles comprising silica and ezetimibe.
Figure 16:
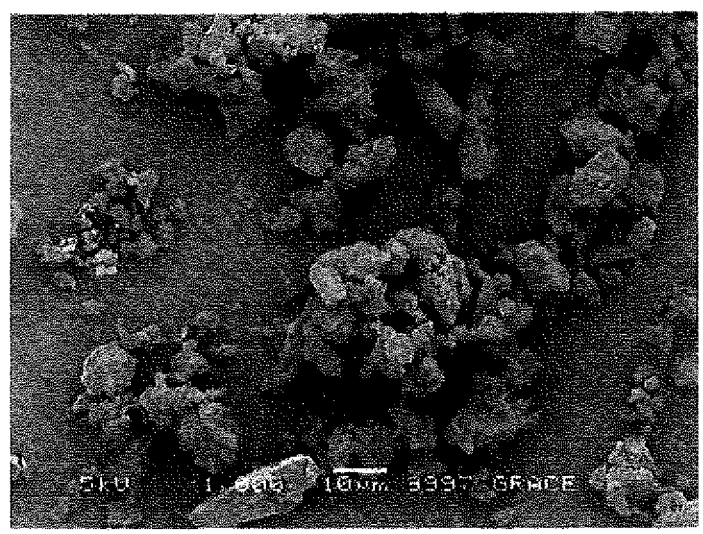

After co-milling, each sample was removed from the vibration chamber and analyzed. FIGS. 15 and 16 depict photographs of composite particles (at a magnification of 1000) similar to those formed in Example 2, namely, composite particles comprising (1) SYLOID® XDP silica and ezetimibe (Sample 12, FIG. 15) and (2) SYLOID® XDP 3050 silica and ezetimibe (Sample 11, FIG. 16).

Figure 17:
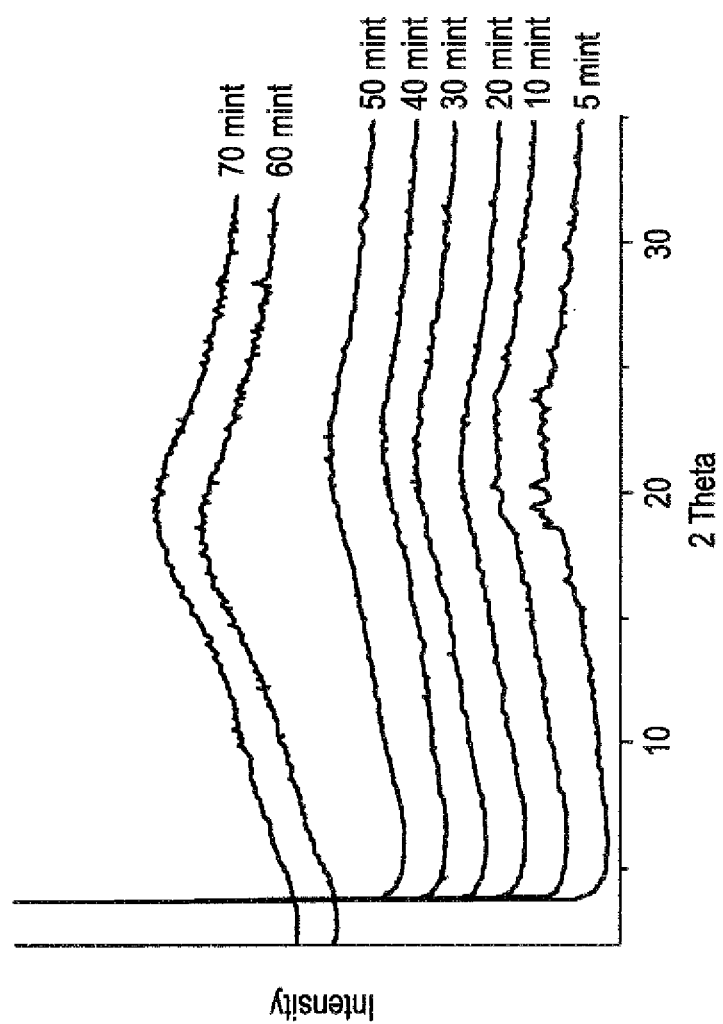
FIG. 17 graphically shows X-ray diffraction data for combinations of ezetimibe co-milled with SYLOID® XDP silica at various milling times.

As shown in FIG. 17, X-ray diffraction data for combinations of ezetimibe co-milled with SYLOID® XDP silica at various milling times indicated conversion of the composite particle component combinations from a crystalline state (i.e., as indicated by sharp peaks along a given plot, e.g., the plot corresponding to the 5 minute trial) to an amorphous state (i.e., as indicated by a smoother plot with less sharp peaks along a given plot, e.g., the plot corresponding to the 50 minute trial).

Figure 18:
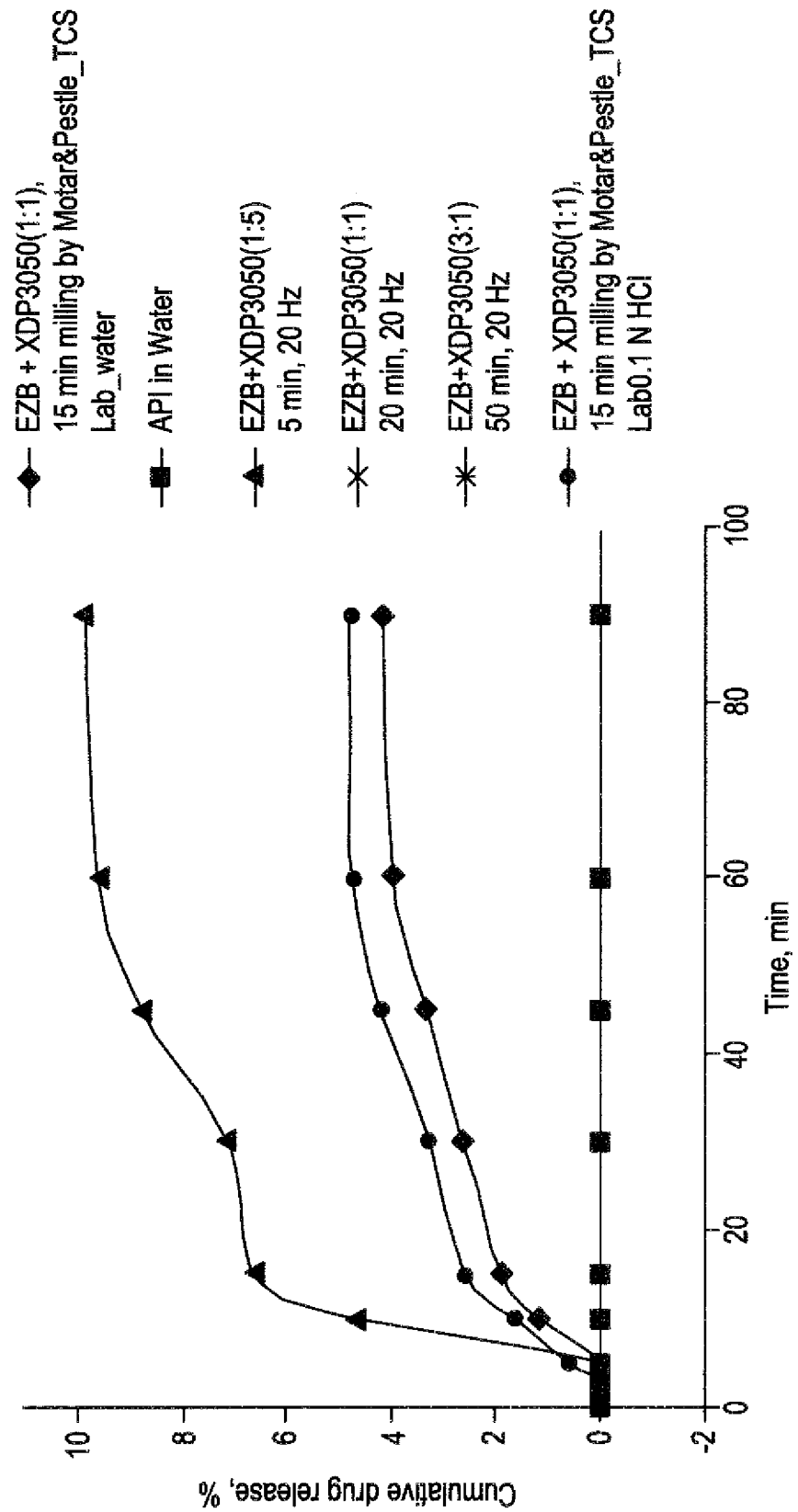
FIG. 18 graphically shows the dissolution of (i) tablets formed with composite particles comprising ezetimibe co-milled with SYLOID® XDP silica, and (iii) commercially available ezetimibe tablet as discussed in Example 2.

FIG. 18 graphically shows the dissolution of (i) ezetimibe alone versus (ii) ezetimibe co-milled with SYLOID® XDP silica as described in Example 2 above. Samples C9 (co-milled 15 min with Mortar and Pestle in water), C10 (unmilled EZB in water), 11 (co-milled 5 min), 12 (co-milled 20 min), 13 (co-milled 50 min) and C11 (co-milled 15 min with Mortar and Pestle in HCl) are shown in FIG. 18. As shown in FIG. 18, composite particles of the present invention (i.e., Sample 11) outperformed all of the remaining samples with regard to drug dissolution.

In summary, in this example, factors including, but not limited to, drug loaded of the composite particle, frequency used, milling time used, and solvent versus solventless systems, were shown to impact the drug dissolution of the resulting composite particles. It is believed that the parameters used to form Sample 11 resulted in crystalline drug amorphonisation during the co-milling process, while different process parameters (e.g., used in Samples 12-13) did not result in crystalline drug amorphonisation.

Example 3: Formation of Composite Particles Comprising Silica and Ibuprofen

Composite particles were prepared using the procedure and materials described in Example 1. Composite particle composition components were used as shown in Table 6 below.

TABLE 4

Composite Particle Compositions

| Material | Sample | | | | | | | | |
|---|---|---|---|---|---|---|---|---|---|
| | C8 | 8 | 9 | C9 | C10 | 11 | 12 | 13 | C11 |
| | Amount (mg) | | | | | | | | |
| SYLOID ® XDP 3050 silica | | 250 | 250 | 250 | | 417 | 250 | 125 | 250 |
| ezetimibe | 500 | 250 | 250 | 250 | 500 | 83 | 250 | 375 | 250 |
| PEG | | | 500 | 250 | | | | | |
| SLS | | | | 250 | | | | | |

Ibuprofen was added to the vibration chamber.

The vibration mill was set at a given frequency and run for a milling time as shown in Table 7 below.

TABLE 6

Composite Particle Compositions

| Material | Sample | | | | | | | | | | | | |
|---|---|---|---|---|---|---|---|---|---|---|---|---|---|
| | C12 | 14 | 15 | 16 | 17 | 18 | C13 | 19 | 20 | 21 | 22 | 23 | 24 |
| | Amount (mg) | | | | | | | | | | | | |
| SYLOID ® 244 FP silica | 500 | 500 | 375 | 375 | 375 | 375 | | | | | | | |
| SYLOID ® XDP3050 silica | | | | | | | 500 | 500 | 375 | 375 | 375 | 375 | 400 |
| ibuprofen | | 125 | 125 | 125 | 125 | | | 125 | 125 | 125 | 125 | 125 | 100 |

TABLE 7

Process Parameters

| Parameter | Sample | | | | | | | | | | | | |
|---|---|---|---|---|---|---|---|---|---|---|---|---|---|
| | C12 | 14 | 15 | 16 | 17 | 18 | C13 | 19 | 20 | 21 | 22 | 23 | 24 |
| frequency (Hz) | — | 30 | 30 | 30 | 30 | 20 | — | 30 | 30 | 30 | 30 | 20 | 20 |
| milling time (minutes) | — | 60 | 30 | 60 | 90 | 60 | — | 60 | 30 | 60 | 90 | 60 | 5 |

Each sample was evaluated for (i) total pore volume, as determined by mercury intrusion porosimetry, and (ii) intra-particle pore volume, as determined by mercury intrusion porosimetry, wherein the intra-particle pores are defined as pores having a pore size of less than or equal to 2200 Å. The results are shown in Table 8 below.

TABLE 8

Total Pore Volume and Intra-Particle Pore Volume

| Sample | Total Pore Volume (ml/g) | Intra-Particle Pore Volume (ml/g) | Particle Equilibrium |
|---|---|---|---|
| C12 | 5.94 | 1.7 | — |
| 14 | 0.76 | 0.16 | yes |
| 15 | 0.92 | 0.20 | yes |
| 16 | 0.34 | 0.09 | yes |
| 17 | 0.76 | 0.20 | yes |
| 18 | 1.16 | 0.30 | no |
| C13 | 2.14 | 1.63 | — |
| 19 | 0.76 | 0.21 | yes |
| 20 | 0.93 | 0.19 | yes? |
| 21 | 0.30 | 0.11 | yes |
| 22 | 0.69 | 0.24 | yes |
| 23 | 0.82 | 0.17 | yes? |
| 24 | 1.27 | 0.48 | no |

Figure 19A:
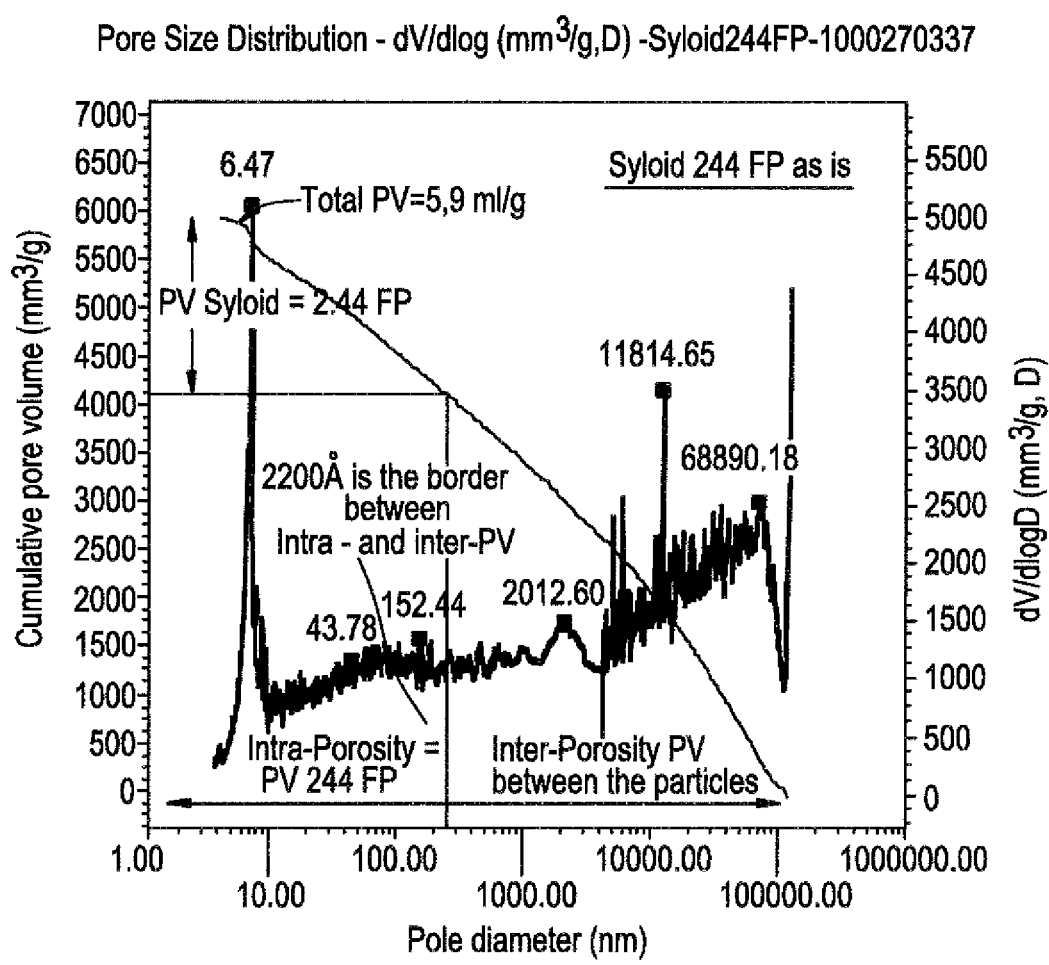
FIGS. 19A-19B depict graphs showing the cumulative pore volume of SYLOID® 244FP silica prior to milling (i.e., FIG. 19A) and after milling (i.e., FIG. 19B, Sample 17 of Example 3).
Figure 19B:
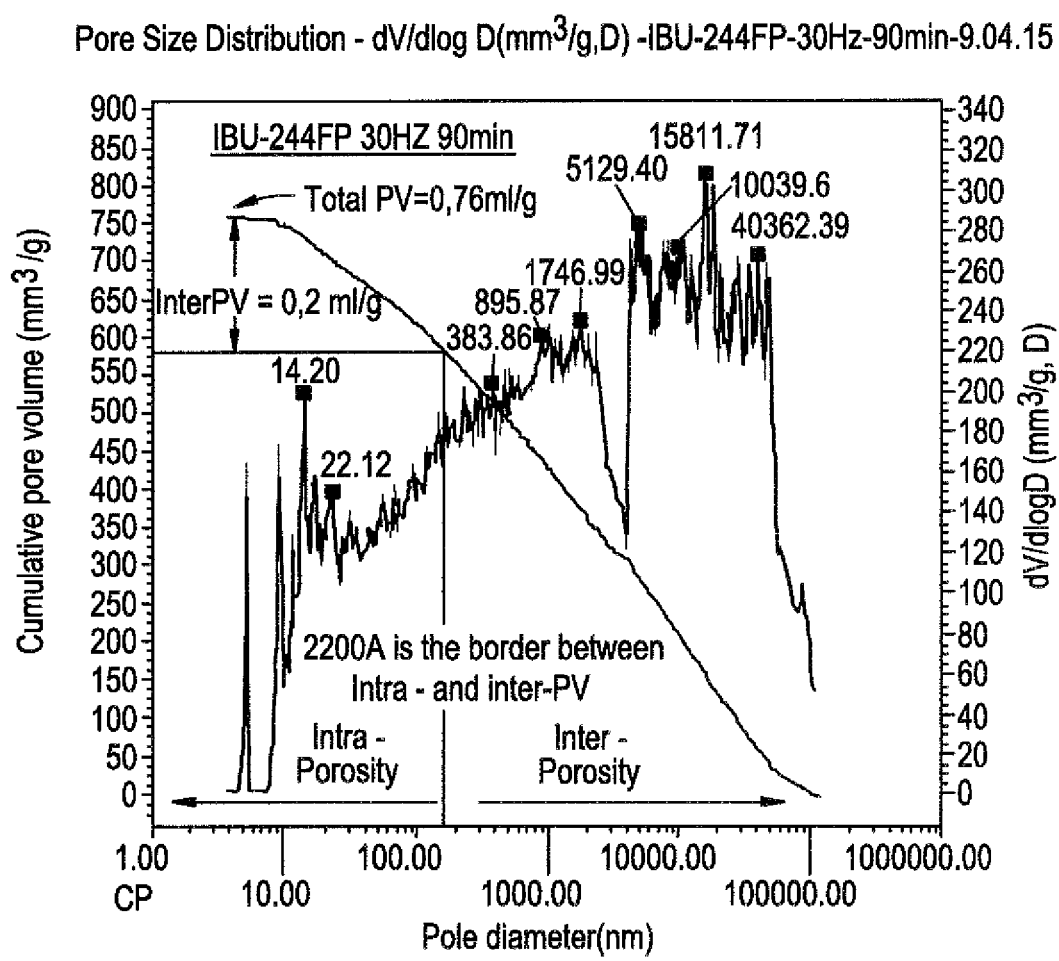

FIGS. 19A-19B depict graphs showing the cumulative pore volume of SYLOID® 244FP silica prior to milling (i.e., FIG. 19A) and after milling (i.e., FIG. 19B, Sample 17 of Example 3).

While the invention has been described with a limited number of embodiments, these specific embodiments are not intended to limit the scope of the invention as otherwise described and claimed herein. It may be evident to those of ordinary skill in the art upon review of the exemplary embodiments herein that further modifications, equivalents, and variations are possible. All parts and percentages in the examples, as well as in the remainder of the specification, are by weight unless otherwise specified. Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 3%, 4%, 5% . . . 50%, 51%, 52% . . . 95%, 96%, 97%, 98%, 99%, or 100%. Moreover, any numerical range represented by any two values of R, as calculated above is also specifically disclosed. Any modifications of the invention, in addition to those shown and described herein, will become apparent to those skilled in the art from the foregoing description and accompanying drawings. Such modifications are intended to fall within the scope of the appended claims. All publications cited herein are incorporated by reference in their entirety.

What is claimed is:

1. Composite particles comprising porous silica gel particles and at least one particulate active ingredient mechanically incorporated in pores of the porous silica gel particles, wherein the composite particles have (i) a total pore volume of less than 1.0 cc/gm, as determined by mercury intrusion porosimetry, and (ii) an intra-particle pore volume of less than 0.3 cc/gm, as determined by mercury intrusion porosimetry, and wherein (a) the intra-particle pores are defined as pores within the composite particles and having a pore size of less than or equal to 2200 Å, and (b) the total pore volume is defined as a combination of (1) an inter-particle pore volume of the composite particles, the inter-particle pore volume being volume between composite particles, and (2) the intra-particle pore volume of the composite particles, wherein the porous silica gel particles comprise newly exposed internal inorganic particle surfaces, the at least one particulate active ingredient comprises newly exposed internal active ingredient particle surfaces, and the at least one particulate active ingredient is in contact with the porous silica gel particles via (i) the newly exposed internal inorganic particle surfaces, (ii) the newly exposed internal active ingredient particle surfaces, or (iii) both (i) and (ii); and wherein the porous silica gel particles and the at least one particulate active ingredient are present at a weight ratio of porous silica gel particles to the at least one active ingredient from about 2:1 to 1:2.

2. The composite particles of claim 1, wherein the composite particles have (i) a total pore volume of greater than 0 and less than about 0.98 cc/gm, as determined by mercury intrusion porosimetry, and (ii) an intra-particle pore volume of greater than 0 and less than about 0.28 cc/gm, as determined by mercury intrusion porosimetry.

3. The composite particles of claim 1, wherein the composite particles have an average particle size of from about 1.0 µm to about 100 µm.

4. The composite particles of claim 1, wherein (i) the porous silica gel particles comprise an agglomeration of the porous silica gel particles having the newly exposed internal inorganic particle surfaces, and (ii) the at least one particulate active ingredient is in contact with said newly exposed internal inorganic particle surfaces.

5. The composite particles of claim 1, wherein the porous silica gel particles have a mean pore diameter of about 1.0 nm to about 100.0 nm.

6. The composite particles of claim 1, wherein the porous silica gel particles have a BET particle surface area of at least about 100 $m^2/g$ up to 1500 $m^2/g$.

7. The composite particles of claim 1, wherein the at least one particulate active ingredient comprises an active pharmaceutical ingredient (API), an agricultural chemical, a food additive, or any combination thereof.

8. The composite particles of claim 7, wherein the at least one particulate active ingredient comprises an active pharmaceutical ingredient (API) having an initial crystalline structure.

9. The composite particles of claim 7, wherein the at least one particulate active ingredient comprises an active pharmaceutical ingredient (API) selected from ibuprofen, ezetimibe, or any combination thereof.

10. The composite particles of claim 1, wherein the porous silica gel particles have a BET particle surface area of at least about 100 $m^2/g$ up to 500 $m^2/g$.

11. The composite particles of claim 1, wherein said composite particles comprise less than about 5.0 wt % water based on a total weight of said composite particles.

12. The composite particles of claim 1, wherein said porous silica gel particles are formed by mechanically altering, via a milling or extrusion step, porous silica gel particles having an initial total pore volume, prior to the mechanically altering, of greater than 1.0 cc/gm, as measured by mercury intrusion porosimetry.

13. A pharmaceutical composition comprising the composite particles of claim 1.

14. The pharmaceutical composition of claim 13, in a form selected from a pill, a tablet, and a capsule.

15. The composite particles of claim 1, wherein the composite particles have (i) a total pore volume of from about 0.15 to about 0.93 cc/gm, as determined by mercury intrusion porosimetry, and (ii) an intra-particle pore volume of from about 0.05 to about 0.24 cc/gm, as determined by mercury intrusion porosimetry.

16. The composite particles of claim 1, wherein the composite particles have (i) a total pore volume of from about 0.25 to about 0.40 cc/gm, as determined by mercury intrusion porosimetry, and (ii) an intra-particle pore volume of from about 0.08 to about 0.16 cc/gm, as determined by mercury intrusion porosimetry.

* * * * *